United States Patent
Chaput et al.

(10) Patent No.: US 8,747,899 B2
(45) Date of Patent: *Jun. 10, 2014

(54) INJECTABLE IN SITU SELF-FORMING MINERAL-POLYMER HYBRID COMPOSITION AND USES THEREOF

(75) Inventors: Cyril Chaput, Montreal (CA); Abdellatif Chenite, Kirkland (CA)

(73) Assignee: Piramal Healthcare (Canada) Ltd., Aurora (CA)

(*) Notice: Subject to any disclaimer, the term of this patent is extended or adjusted under 35 U.S.C. 154(b) by 1110 days.

This patent is subject to a terminal disclaimer.

(21) Appl. No.: 12/575,788

(22) Filed: Oct. 8, 2009

(65) Prior Publication Data
US 2010/0021545 A1    Jan. 28, 2010

Related U.S. Application Data

(63) Continuation of application No. 10/149,053, filed as application No. PCT/CA00/01492 on Dec. 8, 2000, now abandoned.

(60) Provisional application No. 60/169,954, filed on Dec. 9, 1999.

(51) Int. Cl.
    *A61K 9/14*    (2006.01)
(52) U.S. Cl.
    USPC ........................................... 424/484
(58) Field of Classification Search
    None
    See application file for complete search history.

(56) References Cited

U.S. PATENT DOCUMENTS

| | | | |
|---|---|---|---|
| 4,097,935 A * | 7/1978 | Jarcho | 623/23.61 |
| 4,185,618 A | 1/1980 | Corey | |
| 4,195,175 A | 3/1980 | Peniston et al. | |
| 4,267,313 A | 5/1981 | Sannan et al. | |
| 4,391,909 A | 7/1983 | Lim | |
| 4,394,373 A | 7/1983 | Malette et al. | |
| 4,424,346 A | 1/1984 | Hall et al. | |
| 4,474,769 A | 10/1984 | Smith | |

(Continued)

FOREIGN PATENT DOCUMENTS

| | | |
|---|---|---|
| EP | 0 298 501 A2 | 1/1980 |
| EP | 0 640 647 A2 | 3/1995 |

(Continued)

OTHER PUBLICATIONS

Aerts et al., *Journal of Biomechanics*, 28(11):1299-1308 (1995).

(Continued)

*Primary Examiner* — Paul Dickinson
(74) *Attorney, Agent, or Firm* — Nixon Peabody LLP; David S. Resnick; Leena H. Karttunen Contarino

(57) ABSTRACT

Self-forming hybrid compositions consisting in admixed liquid and solid components enable the formation of bio-materials. The present invention proposes a) a thermo-sensitive self-forming liquid component, being water-based and containing at least a polycationic polymer such as chitosan, and an organic mono-phosphate source, which is a solution at a pH ranging from 6.5 to 7.4; b) a solid component being mineral and composed of at least one of calcium, fluoride, strontium, carbonate and phosphate salts. Solid mineral salts preferentially have a recognized bioactive potential such as the calcium phosphate salts for bones. Both solid and liquid components are admixed to form an injectable liquid slurry or pre-gelled paste that turn in situ into a hybrid uniform gel-like bio-material.

44 Claims, 19 Drawing Sheets

(56) References Cited

U.S. PATENT DOCUMENTS

| | | |
|---|---|---|
| 4,647,536 A | 3/1987 | Mosbach |
| 4,659,700 A | 4/1987 | Jackson |
| 4,678,470 A | 7/1987 | Nashef et al. |
| 4,731,081 A | 3/1988 | Tiffany et al. |
| 4,803,075 A | 2/1989 | Wallace et al. |
| 4,895,724 A | 1/1990 | Cardinal et al. |
| 4,956,350 A | 9/1990 | Mosbey |
| 4,996,307 A | 2/1991 | Ito et al. |
| 5,071,644 A | 12/1991 | Viegas et al. |
| 5,073,202 A | 12/1991 | Wallach et al. |
| 5,126,141 A | 6/1992 | Henry |
| 5,204,382 A * | 4/1993 | Wallace et al. ............... 523/115 |
| 5,266,326 A | 11/1993 | Barry et al. |
| 5,278,201 A | 1/1994 | Dunn et al. |
| 5,318,780 A | 6/1994 | Viegas et al. |
| 5,368,051 A | 11/1994 | Dunn et al. |
| 5,422,116 A | 6/1995 | Yen et al. |
| 5,468,787 A | 11/1995 | Braden et al. |
| 5,489,401 A | 2/1996 | Freeman |
| 5,587,175 A | 12/1996 | Viegas et al. |
| 5,599,552 A | 2/1997 | Dunn et al. |
| 5,612,028 A | 3/1997 | Sackier et al. |
| 5,618,339 A | 4/1997 | Ito |
| 5,620,706 A | 4/1997 | Dumitriu et al. |
| 5,655,546 A | 8/1997 | Halpern |
| 5,658,593 A | 8/1997 | Orly et al. |
| 5,683,461 A * | 11/1997 | Lee et al. ..................... 424/423 |
| 5,709,854 A | 1/1998 | Griffith-Cima et al. |
| 5,723,331 A | 3/1998 | Tubo et al. |
| 5,736,372 A | 4/1998 | Vacanti et al. |
| 5,749,874 A | 5/1998 | Schwartz |
| 5,770,193 A | 6/1998 | Vacanti et al. |
| 5,770,417 A | 6/1998 | Vacanti et al. |
| 5,773,033 A | 6/1998 | Cochrum et al. |
| 5,773,608 A | 6/1998 | Yen et al. |
| 5,811,094 A | 9/1998 | Caplan et al. |
| 5,820,608 A | 10/1998 | Luzio et al. |
| 5,837,235 A | 11/1998 | Mueller et al. |
| 5,842,477 A | 12/1998 | Naugnhton et al. |
| 5,843,156 A | 12/1998 | Slepian et al. |
| 5,855,619 A | 1/1999 | Caplan et al. |
| 5,866,415 A | 2/1999 | Villeneuve |
| 5,871,985 A | 2/1999 | Aebischer et al. |
| 5,894,070 A | 4/1999 | Hansson et al. |
| 5,902,741 A | 5/1999 | Purchio et al. |
| 5,902,798 A | 5/1999 | Gouda et al. |
| 5,906,934 A | 5/1999 | Grande et al. |
| 5,908,784 A | 6/1999 | Johnstone et al. |
| 5,944,754 A | 8/1999 | Vacanti |
| 5,958,443 A | 9/1999 | Viegas et al. |
| 5,977,330 A | 11/1999 | Lohmann et al. |
| 6,005,161 A | 12/1999 | Brekke et al. |
| 6,060,534 A | 5/2000 | Ronan et al. |
| 6,080,194 A | 6/2000 | Pachence et al. |
| 6,110,209 A | 8/2000 | Stone |
| 6,124,273 A | 9/2000 | Drohan et al. |
| 6,136,334 A | 10/2000 | Viegas et al. |
| 6,179,872 B1 | 1/2001 | Bell et al. |
| 6,200,606 B1 | 3/2001 | Peterson et al. |
| 6,344,488 B1 | 2/2002 | Chenite et al. |
| 6,372,257 B1 | 4/2002 | Marchosky |
| 6,417,247 B1 | 7/2002 | Armstrong et al. |
| 6,610,669 B1 | 8/2003 | Calias et al. |
| 6,649,192 B2 | 11/2003 | Alonso Fernandez et al. |
| 6,706,690 B2 | 3/2004 | Reich et al. |
| 6,743,783 B1 | 6/2004 | Vournakis et al. |
| 6,756,363 B1 | 6/2004 | Nordquist et al. |
| 6,911,212 B2 | 6/2005 | Gertzman |
| 7,045,141 B2 | 5/2006 | Merboth |
| 7,148,209 B2 | 12/2006 | Hoemann et al. |
| 7,320,962 B2 | 1/2008 | Reich et al. |
| 7,368,126 B2 | 5/2008 | Chen et al. |
| 7,459,307 B2 | 12/2008 | Ha et al. |
| 2002/0082220 A1 | 6/2002 | Hoemann et al. |
| 2003/0143274 A1 | 7/2003 | Viegas et al. |
| 2003/0147860 A1 | 8/2003 | Marchosky |
| 2003/0158302 A1 | 8/2003 | Chaput et al. |
| 2003/0199615 A1 | 10/2003 | Chaput et al. |
| 2004/0022859 A1 | 2/2004 | Chen et al. |
| 2004/0024069 A1 | 2/2004 | Chen et al. |
| 2004/0047892 A1 | 3/2004 | Desrosiers et al. |
| 2004/0091540 A1 | 5/2004 | Desrosiers et al. |
| 2006/0018973 A1 | 1/2006 | Kim et al. |
| 2006/0062768 A1 | 3/2006 | Hnojewyj |
| 2006/0193892 A1 | 8/2006 | Furst et al. |
| 2006/0204544 A1 | 9/2006 | Sunwoo et al. |
| 2006/0204581 A1 | 9/2006 | Gower et al. |
| 2006/0293216 A1 | 12/2006 | Klaveness et al. |
| 2007/0014867 A1 | 1/2007 | Kusanagi et al. |
| 2007/0037737 A1 | 2/2007 | Hoemann et al. |
| 2007/0167400 A1 | 7/2007 | Boucher et al. |
| 2007/0254007 A1 | 11/2007 | Bumgardner et al. |
| 2008/0118563 A1 | 5/2008 | Muzzarelli et al. |
| 2008/0200430 A1 | 8/2008 | Bitterman et al. |
| 2008/0248991 A1 | 10/2008 | Dyer et al. |
| 2009/0004276 A1 | 1/2009 | Ben-Shalom et al. |

FOREIGN PATENT DOCUMENTS

| | | |
|---|---|---|
| EP | 1 077 253 A1 | 2/2001 |
| WO | WO 95/25549 | 9/1995 |
| WO | WO 96/02276 | 2/1996 |
| WO | WO 96/39202 | 12/1996 |
| WO | WO 97/33562 | 9/1997 |
| WO | WO 98/22114 | 5/1998 |
| WO | WO 99/04720 | 2/1999 |
| WO | WO 99/07416 A | 2/1999 |
| WO | WO 99/47186 | 9/1999 |
| WO | WO 00/02905 | 1/2000 |
| WO | WO 00/44413 | 8/2000 |
| WO | WO 00/48550 | 8/2000 |
| WO | 01/36000 A1 | 5/2001 |
| WO | WO 01/36000 A1 | 5/2001 |
| WO | WO 01/41822 A1 | 6/2001 |
| WO | 02/00272 A2 | 1/2002 |
| WO | WO 02/40070 A2 | 5/2002 |
| WO | 2004/016297 A1 | 2/2004 |
| WO | 2008/064487 A1 | 6/2008 |

OTHER PUBLICATIONS

Aiba, *Makromol. Chemie*, 194(1):65-75 (1993).
Alexander et al., *Journal of Zoology—London (A)*, 209:405-419 (1986).
Appling et al., *FEBS Letters*, 250(2):541-544 (1989).
Aspden et al., *European Journal of Pharmaceutical Sciences*, 4:23-31 (1996).
Aston et al., *Journal of Bone and Joint Surgery*, 68-B(1):29-35 (1986).
Ateshian, *Journal of Biomechanical Engineering*, 119:81-86 (1997).
Austin et al., *Science*, 212:749-753 (1981).
Back et al., *Biochemistry*, 18(23):5191-5196 (1979).
Balkin, *Neale's Common Foot Disorders: Diagnosis and Management*, 22:387-400 (1997).
Bartone et al., *Journal of Urology*, 140:1134-1137 (1988).
Bellows et al., *Bone and Mineral*, 17:15-29 (1992).
Bennett et al., *Journal of Anatomy*, 171:131-138 (1990).
Bentley et al., *Nature*, 230:385-388 (1971).
Bernkop-Schnurch et al., *Journal of Pharmaceutical Sciences*. 87(4):430-434 (1998).
Blechschmidt, *Foot and Ankle*, 2(5):260-283 (1982).
Boric et al., *The Journal of Bone and Joint Surgery*, 82-B(2):165-166 (2000).
Breinan et al., *The Journal of Bone and Joint Surgery*, 79-A(10):1439-1451 (1997).
Breinan et al., *Journal of Orthopaedic Research*, 18(5):781-789 (2000).
Brittberg et al., *The New England Journal of Medicine*, 331(14):889-895 (1994).
Brittberg et al., *Clinical Orthopaedics and Related Research*, 326:270-283 (1996).

(56) References Cited

OTHER PUBLICATIONS

Buckwalter et al., *The Journal of Bone and Joint Surgery*, 79-A(4):612-632 (1997).
Buschmann et al., *Journal of Orthopaedic Research*, 10(6):745-758 (1992).
Buschmann et al., *Foot and Ankle*, 14(7):389-394 (1993).
Buschmann et al., *Foot and Ankle*, 16(5):254-258 (1995).
Butnariu-Ephrat et al., *Clinical Orthopaedics and Related Research*, 330:234-243 (1996).
Calvo et al., *Colloid and Polymer Science*, 275(1):46-53 (1997) (abstract).
Caplan et al., *Clinical Orthopaedics and Related Research*, 342:254-269 (1997).
Carreño-Gómez et al., *International Journal of Pharmaceutics*, 148:231-240 (1997).
Chenite et al., *Carbohydrate Polymers*, 00:1-9 (2000).
Ciienite et al., *Biomaterials*, 21:2155-2161 (2000).
Chesterman et al., *The Journal of Bone and Joint Surgery*, 50B(1):184-197 (1968).
Childers et al., *Clinical Orthopaedics and Related Research*, 144:114-120 (1979).
Cho et al., *Biomaterials*, 20:2139-2145 (1999).
Chu et al., *Journal of Biomedical Materials Research*, 29:1147-1154 (1995).
Chu et al., *Clinical Orthopaedics and Related Research*, 340:220-229 (1997).
Chung et al., *Calcif Tissue Int.*, 51:305-311 (1992).
Cohen et al., *British Journal of Haemotology*, 31:45-50 (1975).
D'Ambrosia, *Orthopedics*, 10(1):137-142 (1987).
Denuziere et al., *Biomaterials*, 19:1275-1285 (1998).
Depalma et al., *Clinical Orthopaedics and Related Research*, 48:229-242 (1966).
Dillon et al., *J. Biomater. Sci. Polymer Edn.*, 9(10):1049-1069 (1998).
Elçin et al., *Neurological Research*, 20:648-654 (1998).
Frenkel et al., *The Journal of Bone and Joint Surgery*, 79-B(5):831-836 (1997).
Freed et al., *Journal of Biomedical Materials Research*, 28:891-899 (1994).
Fukamizo et al., *Biochem. Cell Biol.*, 75:687-696 (1997).
Gillquist et al., *Acta Orthop Scand.*, 68(2):186-191 (1997).
Grande et al., *Journal of Orthopaedic Research*, 7(2):208-218 (1989).
Green, *Clinical Orthopaedics and Related Research*, 124:237-250 (1977).
Guo et al., *Connective Tissue Research*, 19:277-297 (1989).
Gupta et al., *The International Journal of Artificial Organs*, 16(3):155-163 (1993).
Hangody et al., *Knee Surg., Sports Traumatol., Arthrosc.*, 5:262-267 (1997).
Hangody et al., *Fool and Ankle International*, 18(10):628-634 (1997).
Hendrickson et al., *Journal of Orthopaedic Research*, 12(4):485-497 (1994).
Iiigaki et al., *JSME International Journal*, 40(4):776-781 (1997).
Hirano et al., *Biopolymers*, 15:1685-1691 (1976).
Homminga et al., *Acta Orthop. Scand.*, 62(5):415-418 (1991).
Hunziker et al., *The Journal of Bone and Joint Surgery*, 78-A(5):721-733 (1996).
Hyc et al., *Cell Transplantation*, 6(2):119-124 (1997).
Itay et al., *Cartilage Repair by Cultured Chondrocytes*, 220:284-303 (1987).
Jahss et al., *Foot and Ankle*, 13(5):227-232 (1992).
Johnson, *Operative Arthroscopy*, Chapter 24, pp. 341-360 (1991).
Jürgensen et al., *The Journal of Bone and Joint Surgery*, 79-A(2):185-193 (1997).
Kandel et al., *Art. Cells, Blood Subs., and Immob. Biotech.*, 23(5):565-577 (1995).
Kawamura et al., *Acta Orthop. Scand.*, 69(1):56-62 (1998).
Ker, *Journal of Experimental Biology*, 199:1501-1508 (1996).
Kopp et al., *Int. J. Cancer*, 60:275-279 (1995).
Koyano et al., *J. Biomed. Mater. Res.*, 39:486-490 (1998).
Kubota et al., *Polymer Journal*, 29(2):123-127 (1997).
Kuettner, *Clinical Biochemistry*, 25:155-163 (1992).
Lahiji et al., *J. Biomed. Mater. Res.*, 51:586-595 (2000).
Lee et al., *Journal of Controlled Release*, 51:213-220 (1998).
Lee et al., *J. Periodontol.*, 71(3):410-417 (2000).
Leistikow, *Seminars in Thrombosis and Hemostasis*, 22(3):289-294 (1996).
Li, *Biotechnol. Appl. Biochem.*, 23:269-271 (1996).
Lu et al., *Biomaterials*, 20:1937-1944 (1999).
Mahomed et al., *Orthopedics*, 15(10):1191-1199 (1992).
Malette et al., *The Annals of Thoracic Surgery*, 36(1):55-58 (1983).
Mankin, *The New England Journal of Medicine*, pp. 1285-1292 (1974).
Matthew et al., *Journal of Pediatric Surgery*, 28(11):1423-1428 (1993).
Mattioli-Belmonte et al., *Medical and Biological Engineering and Computing*, 37:130-134 (1999).
Messner et al., *Acta Orthop. Scand.*, 67(5):523-529 (1996).
Minas et al., *Articular Cartilage Defects*, 20(6):525-538 (1997).
Muzzarelli et al., *Biomaterials*, 9:247-252 (1988).
Muzzarelli et al., *Eur. Chitin Soc.*, Ancona (1993).
Muzzarelli et al., *Biomaterials*, 15(13):1075-1081 (1994).
Muzzarelli et al., *Enzyme Microb. Technol.*, 17:541-545 (1995).
Namba et al., *The Journal of Bone and Joint Surgery*, 80-A(1):4-10 (1998).
Narváez et al., *Radiographics*, 20(2):333-352 (2000).
Nevo et al., *Cell Transplantation*, 7(1):63-70 (1998).
Newman, *The American Journal of Sports Medicine*, 26(2):309-324 (1998).
Nixon et al., *Journal of Orthopaedic Research*, 17(4):475-487 (1999).
Noguchi et al., *Clinical Orthopaedics and Related Research*, 302:251-258 (1994).
O'Driscoll et al., *The Journal of Bone and Joint Surgery*, 70-A(4):595-606 (1988).
O'Driscoll et al., *The Journal of Bone and Joint Surgery*, 76-A(7):1042-1051 (1994).
Ohya et al., *J. Microencapsulation*, 10(1):1-9 (1993).
Okamoto et al., *J. Vet. Med. Sci.*, 57(5):851-854 (1995).
Outerbridge et al., *The Journal of Bone and Joint Surgery*, 77-A(1):65-72 (1995).
Paletta et al., *The American Journal of Sports Medicine*, 20(6):725-731 (1992).
Pechak et al., *Bone*, 7:459-472 (1986).
Peluso et al., *Biomaterials*, 15(15):1215-1220 (1994).
Pridie, *The Journal of Bone and Joint Surgery*, 41-B(3):618-619 (1959).
Rao et al., *Journal of Biomedical Materials Research*, 34:21-28 (1997).
Robinson et al., *Calcif Tissue Int.*, 46:246-253 (1990).
Rodrigo et al., *Operative Orthopaedics*, Chapter 144, pp. 2077-2082 (1993).
Sall et al., *Ann. Ophthalmol.*, 19:31-33 (1987).
Sams et al., *Osteoarthritis and Cartilage*, 3:47-59 (1995).
Schipper et al., *Pharmaceutical Research*, 14(7):923-929 (1997).
Schwarz et al., *British Journal of Rheumatology*, 37(1):21-26 (1998).
Sechriest et al., *J. Biomed. Mater Res*, 49(4):534-541 (2000).
Sellers et al., *The Journal of Bone and Joint Surgery*, 79-A(10):1452-1463 (1997).
Sellers et al., *The Journal of Bone and Joint Surgery*, 82-A(2):151-160 (2000).
Senoo et al., Accession No. 25365 (1990) (abstract).
Shepard et al., *XVIIth FECTS Meeting Patras*, Greece, Abstract Form (Jul. 1-5, 2000).
Siiigemasa et al., *Biotechnology and Genetic Engineering Reviews*, 13:383-420 (1995).
Soulhat et al., *Journal of Biomechanical Engineering*, 121:340-347 (1999).
Specchia et al., *Bulletin for Hospital for Joint Diseases*, 54(4):230-235 (1996).
Steadman et al., *J. Sports Traumatol. Rel. Res.*, 20(2):61-70 (1998).
Stone et al., *British Journal of Plastic Surgery*, 53:601-606 (2000).

(56) References Cited

OTHER PUBLICATIONS

Suh et al., *Biomaterials*, 21:2589-2597 (2000).
Terbojevich et al., *Carbohydrate Polymers*, 29(1):63-68 (1996).
Ueno et al., *Biomaterials*, 20:1407-1414 (1999).
Van Schie et al., *Diabetes Care*, 23(5):634-638 (2000).
Vasios et al., *45th Annual Meeting*, Orthopaedic Research Society, Anaheim, California, 711 (Feb. 1-4, 1999).
Wakitani et al., *The Journal of Bone and Joint Surgery*, 71-B(1):74-80 (1989).
Wakitani et al., *The Journal of Bone and Joint Surgery*, 76-A(4):579-592 (1994).
Wei et al., *Journal of Biomedical Materials Research*, 34:63-72 (1997).
Yagi et al., *Biol. Pharm. Bull.*, 20(12):1290-1294 (1997).
Zielinski et al., *Biomaterials*, 15(13):1049-1056 (1994).
Zoppou et al., *Bulletin of Mathematical Biology*, 59(5):953-973 (1997).
Gerstenfeld LC et al., 1987. Expression of differentiated function by mineralizing cultures of chicken osteoblasts. Del Biol 122:49-60.
Sigma-Aldrich Buffer Reference Center. http://www.Sigmaaldrich.com/Area_of_Interest/Biochemicals/Buffer_Explorer/Key_Resources/Buffer_Reference_Center.html accessed Oct. 7, 2005 2 pages.

\* cited by examiner

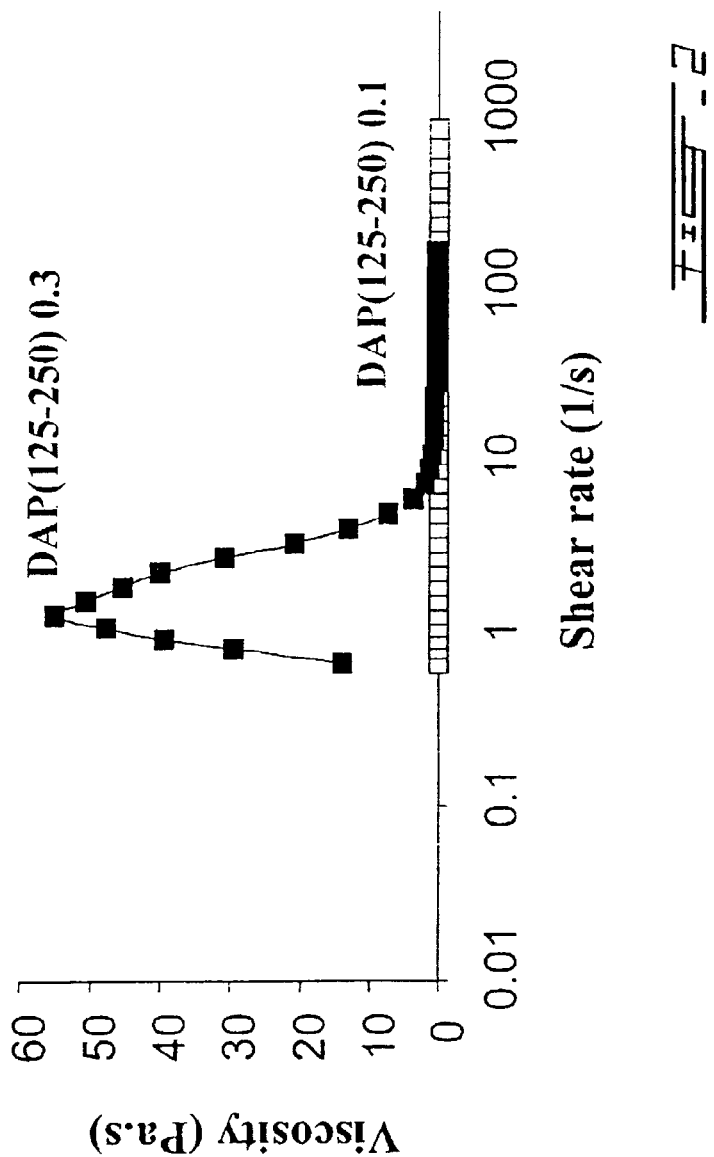

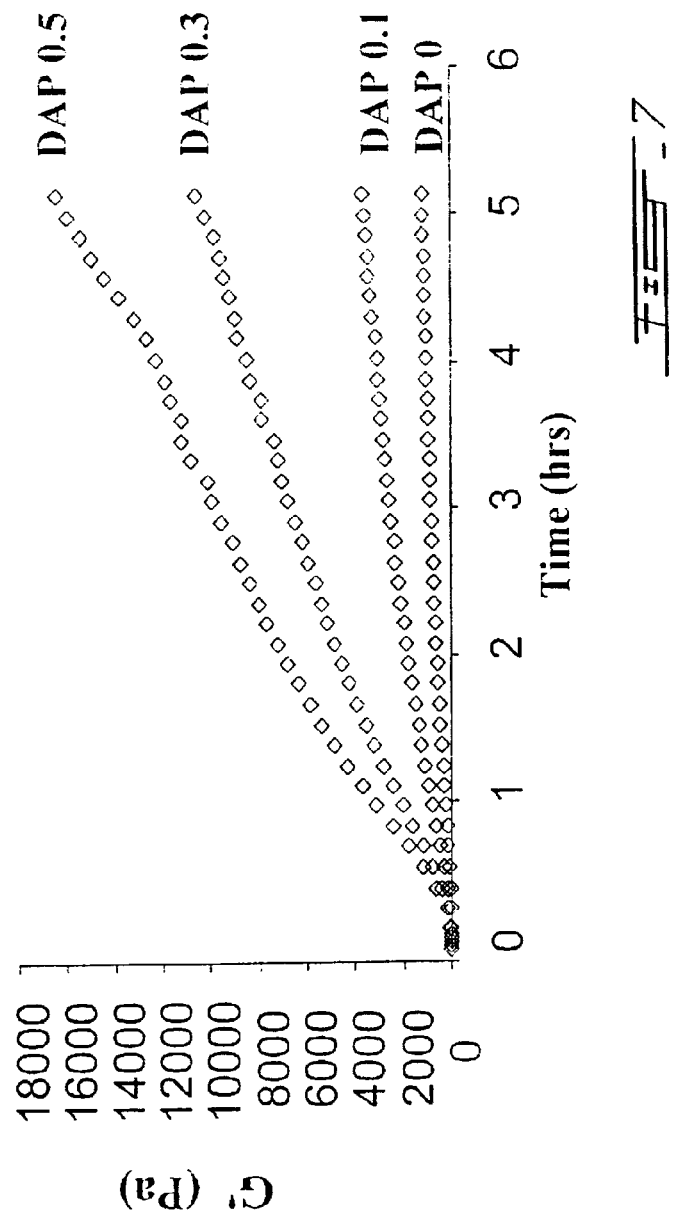

INJECTABLE IN SITU SELF-FORMING MINERAL-POLYMER HYBRID COMPOSITION AND USES THEREOF

BACKGROUND OF THE INVENTION (a) Field of the Invention

The invention relates to the preparation and use of injectable self-forming mineral-polymer hybrid compositions for repairing, replacing or therapeutically treating tissues and body parts. More particularly, the present invention proposes self-gelling mineral-polymer hybrid formulations. More specifically, the present invention comprises self-gelling mineral-polymer hybrid formulations that comprises osteoconductive or osteoinductive agents, drugs or therapeutic and/or healing-accelerator components.

(b) Description of Prior Art

A large quantity of bio-materials have been introduced for hard-tissue repair and formation, including natural or synthetic materials, pure organic or inorganic materials, and organo-inorganic biohybrid or hybrid materials.

Conductive hard-tissue implants are passive bio-materials that provide a matrix to favor and support a new hard-tissue ingrowth and repair. They generally do not provide any osteogenesis property, in the meaning that such materials do not supply, by themselves, any osteogenesis or hard-tissue inductive factors, or any hard-tissue healing accelerators. Conductive structures have typically to favor the own ingrowth and reorganization of hard-tissues (Ex: osteoconductive materials).

The main constituent of hard-tissues is biological apatite that is commonly found in bone and teeth (65-98%). Calcium and phosphate ions are commonly contained in body fluids and mineral contents of hard tissues, including bones, dentine and dental enamel. They may also additionally contain other constituents such as carbonates, magnesium or sodium. Hydroxyapatite is generally recognized as being a calcium phosphate material with a crystal structure very close to biological apatite. Calcium phosphates, and some other ceramics, were found to be very useful biocompatible materials for hard-tissue repair. Today, a large family of ceramic bio-materials having different forms is available for repairing hard-tissues, and includes calcium phosphates, calcium carbonates, bioglasses and pure natural minerals.

Bone Repair and Formation

Conductive matrices for hard-tissue repair are designed to provide adequate compositions and architectures that favors the ingrowth of hard-tissue by its own. These matrices are inserted into a defect, thus contacting mature hard-tissue cells that are capable of invading the repairing matrix and forming mineral networks to complete tissue ingrowth. Typical examples are generally related to osteoconductive materials for bone tissues.

Conductive hard-tissue implants have received a considerable attention, particularly in bone surgery. Grafting materials for defect filling and bone repair include autografts, xenografts, demineralized bone matrix, porous ceramics such as calcium phosphates, calcium carbonates, coral, nacre, bioglasses, organic matrices (polymers, collagen and other biological macromolecules) as well as organo-inorganic biohybrid or hybrid materials such as organo-apatites.

Implants for filling and repairing defects are currently solids, sometimes gels and hydrogels that enable the ingrowth and conduction of the hard-tissue. Porous or plain solids may be used. Plain solid implants stimulate hard-tissue ingrowth through their own resorption. Porosity may be inherent to the material architecture (true porosity), or be interstitial.

Calcium phosphates have been the preferred bone biomaterials. In a large number of animal and human studies, they have been shown to be biocompatible, and bone growth promoters. Targeted calcium phosphate ceramics are tricalcium phosphates, amorphous calcium phosphate, octacalcium phosphate, and apatitic compounds. Hydroxyapatite $[Ca_{10}(PO_4)_6(OH)_2]$, calcium-deficient apatite, fluorinated apatite $[Ca_{10}(PO_4)_6F_2]$, and carbonated apatite $[Ca_{10-x}Ha_x(PO_4)_{6-x}(CO_3)_x(OH)_2]$ are the most representative apatitic compounds. Synthetic or sintered apatites may be prepared.

Most calcium phosphate ceramics are prepared as granules or block materials. Block materials can be prepared with various geometries such as rods, cylinders, rectangular shapes, etc. However, ceramic blocks must be re-shaped before implantation to fit exactly the defect size and geometry, which makes heavier and longer the handling and clinical application. Furthermore, calcium phosphate blocks are very brittle and difficult to shape, and consequently the interface between the bone tissue and ceramic implant is not perfectly continuous which may impair the osteoconduction efficiency. Calcium phosphate granules are currently produced with a wide size distribution, and available from 10 microns to 2.5 mm, but preferably used with a size between 90 and 400 microns. Granules can be injected, or at least administered through less invasive techniques, so as to fulfill the tissue defect. But granules have a mobility problem in situ, which limits their use and efficiency.

Ceramics such as calcium carbonates, coral or nacre are equally proposed under granular or block form, and present similar problems. Bioglasses are generally under granular or microspheric form (Bioglass®, USBio-materials; Biogran®, Orthovita; Perioglass®).

Typical commercial ceramic materials used as osteoconductive materials are for example apatite such as SurgiBone® (Unilab), Osteogen® HA Resorb (Impladent), Periograf®, Alveograft®, ProOsteon® (Interpore), Cerapatite® (Ceraver-Osteal), Ossatite® (MCP), Synatite® (SBM), Ceros®, Interpore® 200 (Interpore), OrthoMatrix™ HA-1000™ and HA-500™, Bio-Oss® (Osteohealth), Calcitite 2040®, Ceros 80® (Matthys), Durapatite®, Apafil-G® (Biomat), HAP Coralina®, Endobon® (Merk), Pyrost® (Osteo), or tricalcium phosphate such as Ceros 82®, Synthograft®, Bioresorb® (SBM), Calciresorb® (Ceraver-Osteal), or a mixture of hydroxyapatite and tricalcium phosphate (biphasic calcium phosphate) such as Triosite® (Zimmer), Ceraform® (Teknimed), Eurocer® (Bioland), BCP® (Bioland), Ostilit® (Howmedica), or coral such as BioCoral® (Inoteb).

Collagen, a component of soft- and hard-tissues, and Bone Demineralized Matrix (BDM) are the current organic materials for filling hard-tissue defects. Collagen was associated with mineral to form hybrid materials such as Collagraft® (NeuColl), Cerapatite-Collagen® (Ceraver-Osteal), Ossatite® composite (MCP) or Collapat® (Osteo).

Polymeric materials such as polylactic acid, polyglycolic acid, polylactic-co-glycolic acid microspheres, and the like, were also proposed for bone defect filling and repair, but are less current than calcium phosphate granular materials. One new development is Immix® (Osteobiologics) bone grafting material based on polylactic acid/glycolic acid (PLA/GA).

Osteoinduction

Osteogenesis factors are generally supplied by surrounding living tissues and blood supply in the vicinity of the hard-tissue implant. It would be highly desirable to propose a hard-tissue repair matrix that combines the ingrowth promotion of newly-formed hard-tissue tissue and the inductive action, for example, an implant material that allows osteoconduction and osteoinduction. The exact mechanism of hard-tissue formation is complex and not perfectly understood, but it is clear that a certain number of biochemical factors are involved in hard-tissue formation and mineralization. Repair of hard-tissues is induced by the maturation of progenitor cells into the expected functional tissue cells. For bone, osteogenesis is reached when osteoprogenitor cells are converted into bone cells that are active to form mineralization and bone tissues. It can be stated that osteogenesis can be obtained in situ through different actors: a) the osteoprogenitor cells that once converted will form bone repairing-forming cells; b) the inductive biochemical environment that will stimulate the conversion and maturation of osteoprogenitor cells and modulate the bone formation and repair response; and c) the conductive bone repairing matrix that will support the formation of new bone tissues and mineralized networks.

Osteogenic stimulation can be first elicitated by bone progenitor cells (osteoprogenitors). Marrow Stroma Cells (MSCS) are recognized as being the precursor cells of hard and connective tissues. Hematopoietic stem cells from bone marrow are also providers of osteoprogenitor cells and promoters of osteogenesis. The injection of bone marrow preparations, with or without carriers, has been described to stimulate osteogenesis and bone repair. The ability of bone marrow to form bone is well-known, and clinically used. Administration of bone marrow through demineralized bone matrix, collagen or hydroxyapatite materials is also observed for repairing bone defects. Retransplantation of MSCs into poorly healing bone is currently viewed as potentially enhancing the repair process.

Cytokines are bioactive proteins that act on cells adjacent to the cell where is it elaborated. Cytokines and bone proteins have been intensively studied in terms of inductive or healing accelerating effects on hard-tissues, and especially on bone, including "bone-derived osteogenesis proteins" (bOP), "bone morphogenic proteins" (BMP) and "growth and differentiation factors" (GDF). BMPs and GDFs from the Transforming Growth Factor-beta gene super-family have been extensively investigated and used for bone formation and repair. Transforming Growth Factor-beta (TGF-beta), Fibroblast Growth Factors (FGF, a-b), and Platelet-Derived Growth Factors (PDGF, A-B) have been proven useful during fracture healing, thus acting at different steps of fracture healing, including the initial injury response, the intramembraneous ossification, the chondrogenesis or the endochondreal ossification.

Commercial developments in osteoinductive or osteoregulating agents comprise rhBMP-2 (Genetic Institute), Ne-Osteo (Sulzer Orthopedics, Biologics), OP-1 (Stryker Biotech), Indian Hedgehog inducing molecule (Ontogeny) and Plasmid DNA (Matrigen).

One key-step in using biological inductive actors is the clinical administration and dosing. Furthermore, bio-materials development for reaching minimally-invasive administration, easiness of application and optimal induction-conduction of hard-tissues is still running, and is a matter of great interest.

The administration to bone of DNA or genetically-modified cells such as MSCs are potential avenues to treat durably hard-tissue deficiencies. When released in-situ, DNA is taken up by the granulation cells which become drug dispensing agents and stimulate formation of hard-tissues. DNA can be dispensed during the granulation component of healing, thus enabling the control of the protein expression for days and weeks and allowing a control of the sequence of events that normally take place in hard-tissue formation. It may be particularly attractive for patients with hard-to-heal fractures or imperfect bone healing. Genetic reprogramming of MSCs so as to express specific proteins may be used therapeutically for hard-tissues as well as for other connective tissues as in the case of deficiencies in circulating proteins. Re-transplantation of genetically-modified MSC cells is a way to control or cure diseases at the genetic level.

Diseases and/or deficiencies associated to hard-tissues may necessitate both a filling, a repair and a local therapeutic treatment, e.g. a partial resection of bone tissue and/or a localized application of therapeutics. Antibiotic, anti-inflammatory, anticancer, antiviral, antimicrobial and/or antibacterial agents may be administrated to hard-tissue sites, e.g. anticancer/antitumor agents introduced in a defect surgically made for resecting a bone tumor. The agent will act so as to prevent or control the recurrence of the tumor in bone.

Injectable Bone Substitutes

Injectable systems were introduced for healing, repair and formation of bone through less invasive and traumatic techniques such as percutaneous methods. Different bio-material concepts have been proposed, and may be classified as follows: a) the pharmaceutical vehicles for bone treatment (Ex: gels); b) the hybrid bone filling/grafting materials (Ex: injectable ceramic/polymer composites); and c) the self-setting bone substitute (Ex: injectable bone cements).

Hyaluronic acid-based gels were proposed for delivering growth factors (OssiGel™) such as basic FGF, thus acting to accelerate fracture healing. Matrigel and Collagen gels were introduced to support and deliver DNA (gene therapy) for hard-tissues (Matrigen™). Those materials are pure organic vehicles, with no mineral content, and no self-forming action.

Particulate solids made of polymers, ceramics or inorganics are currently known as potential injectable materials for defect filling, and to some extent, carrying and delivering systems for soft- and hard-tissues. But injectable granular materials are highly mobile causing problems in situ.

Injectable hybrid bone materials were proposed from granular solids such as, and particularly with, calcium phosphate ceramics dispersed and homogenized in an organic fluidic matrix. Blood and physiological fluid were currently used as the carrier, but do not form really a matrix. Biological sealants such as the fibrin glue were proposed as a matrix to develop a ceramic composite bone material (Sedel et al., *J. Biomed. Mat. Res.* (*Appl. Biomat.*), 43:38-45, 1998; and Wilson et al., *Bio-materials*, 15:601-608, 1993). Poly(propylene fumarate) [PPF] based matrix was also promoted to carry ceramics and form bone composite materials (Mikos et al., *J. Biomed. Mat. Res.*, 44:314-321, 1999). Gelatin was used similarly in Ossatite® (Medical Calcium Phosphate Laboratories, France) injectable bone product (Griffet et al., *Biomaterials*, 20:511-515, 1999). Cellulosics, and especially cellulosic ethers such as hydroxypropyl methylcellulose (HPMC), are currently investigated as a promising carrier/matrix in injectable bone composite materials (Daculsi et al., *J. Biomed. Mat. Res.*, 47:28-35, 1999; Dupraz et al., *Biomaterials*, 20:663-673, 1999; and Grimandi et al., *J. Biomed. Mat. Res.*, 39:660-666, 1998). Daculsi et al. (U.S. Pat. No. 5,717,006) was promoting cellulosics for processing composite bio-materials that contain 40 to 75% by weight of a mineral content. This mineral content was a blend of hydroxyapatite $[Ca_{10}(PO_4)_6(OH)_2]$ and beta-tricalcium phosphate, or calcium titanium phosphate $[Ca(Ti)_4(PO_4)_6]$.

Injectable hybrid compositions for hard-tissues were proposed (U.S. Pat. No. 5,352,715), where a ceramic matrix comprising particles between 50 and 250 microns was dispersed in the fluid carrier. Fluid carrier and nonceramic compounds were selected from collagen, polyethylene glycol, glycerol or succinylated collagen. Collagen was promoted in many systems (U.S. Pat. No. 4,795,467; and U.S. Pat. No.

5,071,436). Ceramic was generally calcium phosphates such as apatites or tricalcium phosphate (U.S. Pat. No. 6,027,742). Bioactive agents were potentially incorporated in the hybrid composition. Another injectable system was presented by Hench et al. (U.S. Pat. No. 5,840,290), consisting in a suspension of bioglasses in a Dextran aqueous solution. Bioglass particles were 90 to 250 microns in size, consisting in 45S5 (Orthovita) glass composition. Fibrin glue and PPF organic matrices were self-forming in situ, but none of these composites were self-setting or self-hardening materials in situ.

Chitosan was admixed in many liquid components of calcium phosphate cement compositions. Chitosan in citric, malic, or phosphoric acid aqueous medium was the liquid component of a self-setting tricalcium phosphate (TCP) or tricalcium phosphate/tetracalcium phosphate (TCP/TTCP) cement (U.S. Pat. Nos. 5,281,404 and 5,180,426). Chitosan in bone cements or substitutes was also studied in the scientific literature, as reported by Leroux et al. (*Bone*, Vol. 25, No 2, supplement, 1999:31S-34S), Hidaka et al. (*J. Biomed. Mat. Res.*, 46:418-423, 1999), and Ito (*Bio-materials*, 12:41-45, 1991).

Osteoconduction and osteogenic performances of chitosan based materials were reviewed, and applied to bio-materials development. Chitosan with immobilized polysaccharides such as heparin, heparan sulfate, chondroitin sulfate and dextran sulfate was reported for stimulating hard-tissue regeneration by Hansson et al. (International Patent Publication WO96/02259). Osteoinductive compositions were also developed by admixing hydroxyapatite and bone-derived osteoinductive gelatin to chitosan solutions (U.S. Pat. No. 5,618,339).

The osteoconduction and osteogenic performances of chitosan was also investigated in vitro and in vivo (Hidaka et al., *J. Biomed. Mat. Res.*, 46:418-423, 1999; and Klokkevold et al., *J. Periondot.*, 67:1170-1175, 1996).

It would be highly desirable to be provided with an in situ self-forming mineral-polymer hybrid composition containing genetically-modified MSCs for treating specific hard-tissue deficiencies or diseases such as brittle bone disease, osteoporosis, Paget's diseases, dysplasia, osteogenesis imperfecta, and the like.

It would be highly desirable to be provided with self-forming mineral-polymer hybrid compositions that are applied to substances, defects or cavities of (soft- or hard-) tissues, or to any anatomical structures of tissues, or any body cavities, thus enabling the formation in situ of a group of bio-materials having distinct compositions, functions and properties.

SUMMARY OF THE INVENTION

One aim of the present invention is to provide a self-forming mineral-polymer hybrid compositions that are applied to substances, defects or cavities of (soft- or hard-) tissues, or to any anatomical structures of tissues, or any body cavities, thus enabling the formation in situ of a group of bio-materials having distinct compositions, functions and properties.

In accordance with the present invention there is provided a new injectable in situ self-forming mineral-polymer compositions that can be conveniently used for tissue repair, replacement or treatment in mammals or humans. Its simplest form is a polymeric aqueous solution composed of an acid-soluble polymer and a water-soluble organic mono-phosphate source having the special property of being endo-thermally sensitive. It forms the basis of the liquid component of all compositions and resulting materials described in the present invention. This endothermally sensitive property results in intrinsic thermo-gelling property, excluding any use of covalent crosslinking or organic solvent, has been presented by Chaput et al.

In accordance with the present invention there is provided an in situ self-forming mineral-polymer hybrid composition comprising:
 a) a water-based and thermo-gelling liquid component comprising at least one hydrosoluble cationic polymer, one organic mono-phosphate source, and optionally one water-soluble organic mono-sulfonate, mono-sulfate or mono-carboxylate source; said liquid component having a pH between 6.5 and 7.4; and
 b) a water non-soluble solid component comprising at least one of calcium, fluoride, strontium, carbonate and phosphate salts,
wherein said liquid component and solid component are admixed together intimately to form a non-hardening thermo-gelling hybrid composition; said hybrid composition gelling at the body temperature.

The liquid component can be prepared from organic and/or inorganic acids, including malic acid, propionic acid, phosphoric acid, organophosphoric acid, glycerophosphoric acid, lactic acid, hydrochloric acid, ascorbic acid, formic acid, acetic acid, and the like.

The polymer can be a cationic hydrophilic polysaccharide bearing amino groups, including partially-deacetylated chitosans, and pure chitosan.

The polymer can be a partially-deacetylated chitosan with a degree of deacetylation between 30 and 99%.

The liquid component can comprise a second soluble polymer selected among polypeptides, cellulosics and synthetic polymers, including collagen, methyl cellulose, hydroxyethyl cellulose, hydroxypropyl cellulose, hydroxyethyl propylcellulose, hydroxymethyl propylcellulose, poly(ethylene oxide), poly(propylene oxide), poly(ethylene glycol), poly(vinyl pyrrolidone) poly(vinyl alcohol), or derivatives thereof, or a mixture thereof.

The organic mono-phosphate, mono-sulfonate, mono-sulfate and mono-carboxylate sources of said liquid component may have a basic character and a pKa between 6.0 and 7.4.

The organic mono-phosphate source can be selected from the group consisting of $Na_2PO_4C_3H_5(OH)_2$, $Fe_2PO_4C_3H_5(OH)_2$, $K_2PO_4C_3H_5(OH)_2$, $MgPO_4C_3H_5(OH)_2$, $MnPO_4C_3H_5(OH)_2$, $Ca_2PO_4C_3H_5(OH)_2$, $Na_2PO_7C_3H_7$, $Na_2PO_7C_4H_7$, $K_2PO_7C_4H_7$, $NaPO_7C_4H_8$, $K_2PO_7C_4H_8$, $Na_2PO_8C_5H_9$, $K_2PO_8C_5H_9$, $NaPO_8C_5H_{10}$, $KPO_8C_5H_{10}$, $Na_2PO_9C_6H_{11}$, $NaPO_9C_6H_{12}$, $K_2PO_9C_6H_{11}$, $KPOC_6H_{12}$, $Na_2PO_8C_6H_{13}$, $K_2PO_8C_6H_{13}$, $NaPO_8C_6H_{14}$, $KPO_8C_6H_{14}$, $Na_2PO_9C_6H_{12}$, $K_2PO_9C_6H_{12}$, $NaPO_9C_6H_{13}$, $KPO_9C_6H_{13}$, $Na_2PO_8C_{10}H_{11}$, $K_2PO_8C_{10}H_{11}$, $NaPO_8C_{10}H_{12}$, and $KPO_8C_{10}H_{12}$ and the like, and derivatives, or mixtures thereof.

The organic mono-phosphate source can be alpha-glycerophosphate, beta-glycerophosphate, glucose-1-phosphate, glucose-6-phosphate, fructose-1-phosphate, or fructose-6-phosphate salt, or a mixture thereof.

The organic mono-sulfonate source can be N-[carbamoyl-methyl]-2-aminoethanesulfonate (ACES), N,N-bis[2-hydroxyethyl]-2-aminoethane-sulfonate (BES), 3-[N,N-bis(2-hydroxyethyl)amino]-2-hydroxypropane-sulfonate (DIPSO), N-[2-hydroxyethyl]piperazine-N'-3-propane-sulfonate (HEPES), 2-[N-morpholino]ethane-sulfonate (MES), 4-[N-morpholino]-butanesulfonate (MOBS), 3-[N-morpholino]-2-hydroxypropanesulfonate (MOPSO), or N-tris[hydroxymethyl]methyl-2-aminoethanesulfonate (TES), or the like, or a mixture thereof.

The liquid component may further comprise bis[2-hydroxyethyl]iminotris [hydroxymethyl]methane (BIS-TRIS), or Tris[hydroxymethyl]aminomethane (TRIZMA), or the like, or a mixture thereof.

The liquid component may further comprise amino-acid residues or sequences, including histidine (HIS) or lysine (LYS) residues or sequences.

The liquid component may comprise organic polyol ingredient including sugar-polyols, saccharide-polyols and glycols, such as glycerol, mannitol, sorbitol, ethylene glycol oligomers, propylene glycol oligomers, fructose, glucose, maltose, and the like.

The liquid component may comprise water-soluble phosphate or carbonate salts, or a mixture thereof.

The liquid component preferably has an intrinsic viscosity ranging between 5 and 100,000 mPa·s at 21° C.

The liquid component preferably forms a homogeneous solid aqueous gel-like material at a temperature between 25 and 60° C.

The solid component may comprise calcium phosphate, calcium sulfate, calcium carbonate, calcium titanate, calcium acetate, calcium glycerophosphate, calcium gluconate, calcium propionate compounds, or the like, or a mixture thereof.

The solid component can comprise at least one calcium phosphate selected from the group consisting of $Ca(H_2PO_4)_2 \cdot H_2O$, $CaHPO_4 \cdot 2H_2O$, $CaHPO_4$, $CaZn_3(PO_4)_2$, $CaZnPO_4$, $CaNaPO_4$, $Ca_2PO_4Cl$, alpha-$Ca_3(PO_4)_2$, beta-$Ca_3(PO_4)_2$, $Ca_3(PO_4)_2 \cdot H_2O$, $Ca_4(PO_4)_2O$, $Ca_8H_2(PO_4)_6 \cdot 5H_2O$, $Ca_9(HPO_4)(PO_4)_5OH$, $Ca_{10}(PO_4)_6(OH)_{2-2x}O_x$, and $Ca_{10}(PO_4)_6(OH)_2$, and derivatives thereof.

The solid component may comprise hydroxyapatite and tricalcium phosphate.

The solid component can comprise hydroxyapatite and alpha- or beta-tricalcium phosphate, or any combination thereof.

The solid component can comprise from 5 to 95% wt. of hydroxyapatite and 90 to 5% wt. of alpha- or beta-tricalcium phosphate.

The solid component preferably comprises from 45-65% wt. of hydroxyapatite and 35-55% wt. of alpha- or beta-tricalcium phosphate.

The solid component can comprise natural mineral components including hard-tissue, enamel or dental apatite, coral or nacre.

The solid component can additionally comprise a carbonate compound selected from $Na_2CO_3$, $CaCO_3$, $K_2CO_3$, $MgCO_3$, $ZnCO_3$, $Ca_9K(PO_4)_5(CO_3)_2$, $Ca_{8.5}Na_{1.5}(PO_4)_{4.5}(CO_3)_{2.5}$, $Ca_9(PO_4)_{4.5}(CO_3)_{1.5}$, and the like.

The solid component can additionally comprise a carbonated calcium phosphate.

The solid component can additionally comprise a fluoride compound selected from NaF, $Na_2Si_6F$, KF, $KSi_6F$, $CaF_2$, $MgF_2$, $ZnF_2$, sodium fluorophosphates, and the like.

The solid component can additionally comprise a fluorinated calcium phosphate.

The solid component can additionally comprise a strontium compound.

The solid component can additionally comprise a strontium containing calcium phosphate.

The solid component preferably comprises natural or synthetic solid components including mineral or ceramic materials, bioglasses, polymeric or biopolymeric materials, and the like.

The solid component and said liquid component preferably have a solid/liquid weight ratio between 0.05 and 2.0 g/mL.

The solid component can consist in dry ingredients with a size ranging from 5 to 1000 micrometers.

The hybrid composition is preferably at least partly resorbable in situ over time such as over a period of 18 months.

The hybrid composition or liquid component or solid component can be admixed with autologous materials selected from a group comprising cortical or cortico-cancellous bone, whole blood and blood components, bone marrow, cells isolated from tissues, stroma cells, or hematopoietic cells.

The composition of the present invention may further comprise osteoinductive agents selected from the group consisting of growth factors, hormones, individual osteoinductive proteins and mixtures of osteoinductive proteins.

The composition of the present invention may further comprise bone derived materials including demineralized bone matrix (DBM) or powder (DBP).

The composition of the present invention may also further comprise at least one growth factor selected from the group consisting of IGF, EGF, a-FGF, b-FGF, PDGF-A, PDGF-B and TGF-beta.

The composition of the present invention may further comprise at least one bone morphogenic proteins (BMP), sialoproteins, osteonectin, osteopontin, osteocalcin, calcitonin, or a mixture thereof.

The composition of the present invention may also further comprise anti-resorptive, antibiotic, antiviral, antitumor, and/or immunosupressive agent.

In accordance with the present invention, there is provided the use of a composition as defined above as a gelling composition to correct a defect, cavity or interface of a tissue, or in a body cavity, and turned in situ into a gel-like filling material.

The composition may also be used as a gel-like material to fulfill a defect, cavity or interface of a tissue, or in a body cavity.

The hybrid composition is preferably administered and is completely self-formed in a defect, cavity or interface of one or more bones.

The hybrid composition is preferably administered and is completely self-formed in a defect, cavity or interface of a cortical, corticocancellous or cancellous part of a bone.

The hybrid composition can be administered and completely self-formed in a defect, cavity or interface between tissue parts or fragments of a fractured bone.

The hybrid composition can be administered and completely self-formed in a defect, cavity or interface at the metaphyseal or diaphyseal region of a bone.

The hybrid composition can be administered and is completely self-formed in a defect, cavity or interface of a hyaline cartilage tissue.

The hybrid composition can be administered and completely self-formed in a defect, cavity or interface of a fibro-cartilage tissue.

The hybrid composition is preferably injected or extruded percutaneously or endoscopically into a defect, cavity or interface of a tissue or a body cavity through a cannula, catheter, trocar or needle.

The hybrid composition can be applied and gelled during the course of an open surgical operation.

The hybrid composition can be administered during the course of a repairing, reconstructing or replacing treatment in dental, plastic, cranio-maxillofacial or orthopaedic surgery.

In accordance with the present invention, there is provided an in situ self-forming mineral-polymer hybrid composition comprising:
  a) a thermo-gelling liquid component, comprising at least 0.5% w/v of a chitosan, 2.0% w/v of a glycerophosphate; said liquid component having a pH between 6.5 and 7.4; and b) a solid component comprising at least one apatite and one tricalcium phosphate, wherein said liquid component and solid component are admixed together intimately to form a non-hardening thermo-gelling hybrid composition; said hybrid composition gelling at the body temperature.

The liquid component may additionally comprise 0 to 10% w/v of at least one of glycerol, sorbitol, mannitol, ethylene glycol oligomers or polymers, and propylene glycol oligomers or polymers.

The liquid component can be admixed with autologous blood, blood component or bone marrow, said autologous blood, blood component or bone marrow being at a concentration ranging from 0 to 25% w/v.

The solid component is preferably a dry mixture of at least hydroxyapatite and beta-tricalcium phosphate.

The solid component can additionally comprise at least a strontium containing calcium phosphate.

The solid component can additionally comprise 0 to 25% w/v of dry crunched autologous spongy bone.

The solid component can additionally comprise 0 to 55% w/v of dry demineralized bone material.

In accordance with the present invention, there is provided a method of preparation of an in situ self-forming mineral-polymer hybrid composition as described previously. The method comprises the step of:
 a) preparing a first water-based liquid sub-component comprising at least one hydrosoluble cationic polymer, and preferably at least 0.5% w/v of a chitosan, said first sub-component being stable and stored below 10° C.;
 b) preparing a second water-based liquid sub-component comprising at least one organic mono-phosphate source, and optionally one water-soluble organic mono-sulfonate, mono-sulfate or mono-carboxylate source;
 c) preparing a solid component comprising at least one of calcium, fluoride, strontium, carbonate and phosphate salts, such as apatite and one tricalcium phosphate;
 d) admixing homogeneously said second liquid sub-component with said solid component into a stable water-based dispersion, said dispersion being stable and stored at room temperature or below; and
 e) admixing said first liquid component and said stable dispersion together intimately to form a non-hardening thermo-gelling hybrid composition, said hybrid composition having a pH between 6.5 and 7.4, being injectable, gelling at the body temperature and being applicable to any defect, cavity or anatomical structure of body's tissues.

For the purpose of the present invention the following terms are defined below.

In the present invention, the term "endothermally sensitive" solution refers herein to a solution turning into a gel material with an increasing temperature. In that meaning, endothermally sensitive may be easily replaced by "endothermally gelling".

"Hydrosoluble" refers to any chemical or compound that dissolve readily in a water-based (aqueous) medium.

In the present invention, the composition comprises a liquid component and a solid component, such components being intimately mixed together; said liquid component being endothermally sensitive as previously defined.

The term "mineral-polymer composite" refers herein to a biphasic system where a mineral component is associated to a polymer component, whatever said mineral and polymer components are liquid or solid.

The term "liquid component" refers herein to a water-based solution, and particularly a water-based polymeric solution.

The term "solid component" refers herein to a solid material, said solid materials being preferably a powder, particulate, microsphere or granular material. Also used for solid component is a "mineral component".

The term "dry ingredient" refers to a dry solid material that enters in the preparation of the solid component and mineral-polymer hybrid composition. In most cases, it is a solid particulates made of minerals or organics, or a mixture thereof.

"Bioactive agent" refers herein to a substance which presents an established biological activity of interest for the use of the hybrid composition. "Non-bioactive agent" corresponds to any substance used without any consideration for a possible biological activity of the hybrid composition.

"Self-gelling" refers herein to the sol-gel transition associated to the liquid component, resulting in the formation of uniform three-dimensional hydrated network (mainly organic). The self-gelling reaction is a reaction intrinsic to the polymer in the liquid component. Herein, gelling excludes hardening.

The term "Gel-like" refers to a substance which has the appearance of a homogeneous highly-hydrated gel. Gel-like excludes solid in the meaning of poorly or non hydrated solid materials (hard solid).

In the present invention, the term "polycationic" or "cationic polymer" refers to a polymer, natural (biological), artificial or synthetic, that has positively-charged chemical groups. The preferred groups include amines (free amines). Typical polycationics of the invention include non-exclusively polyamines such as poly-lysine, chitosan or polyethyleneimide, or zwitterian polymers such as collagens.

In the present invention, the new in situ self-forming mineral-polymer hybrid composition refers especially to an injectable self-forming mineral-polymer hybrid composition and bio-material wherein the material formation in situ is related to those of gel-like materials; the material formation is related to a sol-gel transition that occurs intrinsically within the liquid component (self-gelling); the compositions or biomaterials are defined herein by "self-gelling mineral-polymer hybrid compositions or bio-materials" or "self-gelling hybrid composition" or "self-gelling composition". This composition can however be used prior to gelling or at a gelled state.

BRIEF DESCRIPTION OF THE DRAWINGS

FIG. 2 illustrates the viscosity of DAP-CGP hybrid systems (chitosan 2% w/v; GP 8.2% w/v) as a function of the shear rate (20° C.);

FIG. 7 illustrates the rheological characteristics of DAP-CGP hybrid systems (chitosan 2% w/v; GP 8.2% w/v), the elastic modulus (G') is given during the gelling (37° C.);

DETAILED DESCRIPTION OF THE INVENTION

Figure 1A:
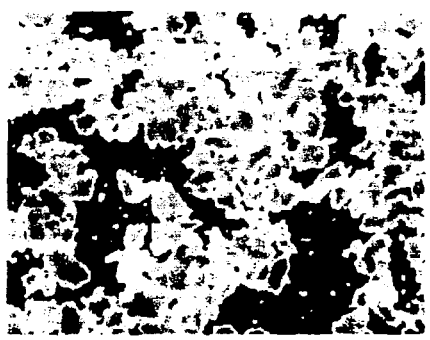
FIG. 1 illustrates a light microscopy view of CaP particulates, such as Durapatite (>125 mic.) (FIG. 1A), Durapatite (125-250 mic.)(FIG. 1B), TCP (FIG. 1C), synthetic HAP (100-300 mic.)(FIG. 1D), Coralline HAP (300 mic)(FIG. 1E) and DAP microspheres (FIG. 1F) that can be incorporated into the CGP systems.
Figure 1B:
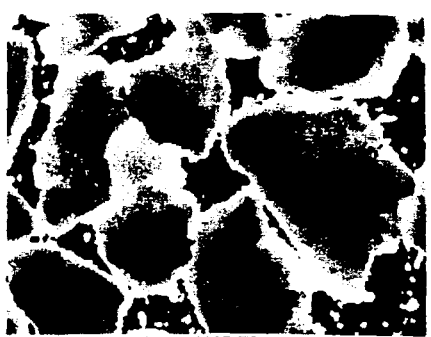
Figure 1C:
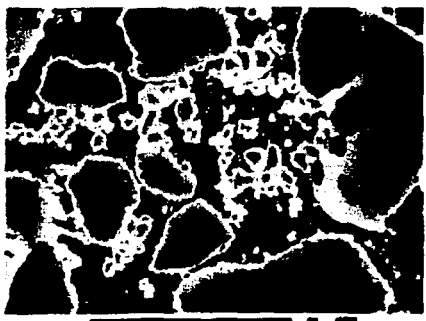
Figure 1D:
Figure 1E:
Figure 1F:
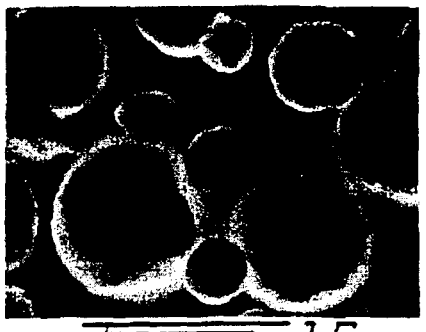

In the invention, self-forming mineral-polymer hybrid compositions are prepared as filling vehicles based mainly upon a self-forming neutral polymeric aqueous composition. They are mainly thermo-gelling polymeric systems, comprising a solid mineral (or ceramic) component, and are first transformed in ceramic/gel-like materials at the body temperature. The polymeric compositions are ideally applied to fill defects, cavities or anatomical structures as well as at the interface with prostheses or implants. This composition carries, osteoconductive materials, osteoinductive agents, drugs, therapeutics and/or healing accelerators such as growth factors, synthetic molecules or tissue proteins.

This composition may have a non-neglectible mineral or ceramic content that may enable mineralization and stimulate formation of hard-tissue minerals, for example by conversion in situ into bone apatite, but it does not self-harden in situ, and must not be considered as a self-setting bio-material. This hybrid composition is administered in situ as an injectable self-gelling liquid slurry or an extrudable hybrid gel-like paste.

Preparation of the Liquid Component

In the invention, the liquid component is an endothermally sensitive solution, and comprises a polymeric aqueous solution. In one embodiment, the liquid component comprises water, an organic and/or inorganic acid, at least one hydrosoluble cationic polymer, and at least one water-soluble phosphate source. In another embodiment, the composition comprises water, an organic and/or inorganic acid, at least one hydrosoluble cationic polymer, at least one water-soluble phosphate source, and at least one water-soluble sulfonate or carboxylate salt. The hydrosoluble cationic polymer is an hydrophilic polymer that has charged cationic groups, and is soluble in an aqueous medium. This polymer is preferably soluble in aqueous media with a pH inferior to 6.5. Typical hydrosoluble cationic polymer includes polysaccharides, for example chitin and chitosan derivatives such as partially-deacetylated chitins and chitosans, non-substituted partially-deacetylated chitins and chitosans, partially-deacetylated chitins and chitosans N-substituted with specific groups such as typically N-alkyl chitosans, N,O-alkylchitosans, N,N-di-alkylchitosans, N-halochitosans, chitosans substituted with hydrophilic groups, etc. Hydrosoluble cationic polymers also comprises those related to polypeptides, collagens and synthetic polymers.

The liquid component is characterized by its endothermal sensitivity which means generally that it presents a sol-gel transition temperature (SGTT), a liquid state (sol state) at a temperature lower than the SGTT, and a gel state In which a gel is substantially water-insoluble at a temperature higher than the SGTT.

In the liquid component, the polymer is dissolved by using organic and/or inorganic acids, including malic acid, propionic acid, phosphoric acid, lactic acid, hydrochloric acid, ascorbic acid, formic acid, acetic acid, and the like. Polyacids such as polyacrylic acid are not used in the present invention. The polymer is dissolved in an acidic aqueous medium having a pH ranging between 1.0 and 5.0, preferentially between 1.0 and 4.0. The polymer is a hydrosoluble cationic polymer, typically a water-soluble hydrophilic polysaccharide bearing amino groups, including chitin, partially deacetylated chitins and chitosan, or an aminated polysaccharides having the desired characteristics. The content in polymer is ranging between 0.1% and 10% w/v, preferentially between 0.5 and 5.0% w/v, and more preferably between 0.5% and 3.0% w/v. The polymer may be optionally combined with another polymer selected from the group consisting of polysaccharides, polypeptides, cellulosics and synthetic polymers, including modified chitin, modified chitosans, collagen, methylcellulose, hydroxyethyl cellulose, hydroxypropylcellulose, hydroxyethyl propylcellulose, hydroxymethyl propylcellulose, poly(ethylene oxide), poly(propylene oxide), poly(vinyl alcohol), and the like, or a mixture thereof. The content in the second polymer varies between 0.01% and 5.0% w/v, preferentially between 0.01% and 2.5% w/v, and more preferably between 0.01% and 1.0% w/v. A typical example of second polymer is N,O-carboxymethyl-chitosan or N,O-glycolic-chitosan, poly(ethylene oxide), poly(ethylene oxide-co-propylene oxide-co-ethylene oxide), or methyl cellulose. In another embodiment, the preferred other polymer is a collagen that is solubilized at a concentration between 0.5 to 10% w/v.

The water-soluble phosphate source of the liquid component is defined as being an organic mono-phosphate basic salt. It has a moderate basic character, and a pKa (referred as being the acidity constant) between 6.0 and 7.4. This phosphate source is preferentially a (di)sodium, (di)potassium, magnesium, manganese or (di)ferric salt, and more preferably a disodium, dipotassium or magnesium salt, or a mixture thereof. The concentration of the phosphate source of the liquid component is between 0.1% and 20% w/v, and ideally between 1.0% and 10% w/v. The said phosphate source is preferably selected in a group comprising $Na_2PO_4C_3H_5(OH)_2$, $Fe_2PO_4C_3H_5(OH)_2$, $K_2PO_4C_3H_5(OH)_2$, $MgPO_4C_3H_5(OH)_2$, $MnPO_4C_3H_5(OH)_2$, $Ca_2PO_4C_3H_5(OH)_2$, $Na_2PO_7C_3H_7$, $Na_2PO_7C_4H_7$, $K_2PO_7C_4H_7$, $NaPO_7C_4H_8$, $K_2PO_7C_4H_8$, $Na_2PO_8C_5H_9$, $K_2PO_8C_5H_9$, $NaPO_8C_5H_{10}$, $KPO_8C_5H_{10}$, $Na_2PO_9C_6H_{11}$, $NaPO_9C_6H_{12}$, $K_2PO_9C_6H_{11}$, $KPO_9C_6H_{12}$, $Na_2PO_8C_6H_{13}$, $K_2PO_8C_6H_{13}$, $NaPO_8C_6H_{14}$, $KPO_8C_6H_{14}$, $Na_2PO_9C_6H_{12}$, $K_2PO_9C_6H_{12}$, $NaPO_9C_6H_{13}$, $KPO_9C_6H_{13}$, $Na_2PO_8C_{10}H_{11}$, $K_2PO_8C_{10}H_{11}$, $NaPO_8C_{10}H_{12}$, $KPO_8C_{10}H_{12}$ and the like, derivatives, or a mixture thereof. Ideally, the phosphate source is alpha or beta glycerophosphate (glycerol-2-phosphate, glycerol-2-phosphate), glucose-1-phosphate, glucose-6-phosphate, fructose-1-phosphate or fructose-6-phosphate disodium or dipotassium, magnesium, or a mixture thereof.

The liquid component may optionally comprise at least one sulfonate source, in a proportion of 0.1 to 10% w/v, selected among N-[carbamoyl methyl]-2-aminoethanesulfonate (ACES), N,N-bis[2-hydroxyethyl]-2-aminoethane-sulfonate (BES), 3-[N,N-bis(2-hydroxyethyl)amino]-2-hydroxypropanesulfonate (DIPSO), N-[2-hydroxyethyl]piperazine-N'-3-propanesulfonate (EPPS), N-[2-hydroxyethyl]piperazine-N'-3-propanesulfonate (HEPES), 2-[N-morpholino]ethanesulfonate (MES), 4-[N-morpholino]butanesulfonate (MOBS), Piperazine-N,N'-bis[2-ethanesulfonate] (PIPES), Piperazine-N,N'-bis[2-hydroxypropane-sulfonate] (POPSO), N-tris[hydroxymethyl]methyl-2-minoethane-sulfonate (TES), and the like, or a mixture thereof.

The liquid component may optionally comprise other molecules such as water-soluble molecules having one acid and at least two amino groups, or more amino groups than acid groups, or at least one amino groups and multiple alcohol groups; said molecules having a moderate basic character and a pKa between 6.0 and 7.4. This molecule is generally selected among amino-acid residues or sequences, including histidine (HIS) or lysine (LYS) residues or sequences, and/or among a group comprising bis[2-hydroxyethyl]iminotris[hydroxymethyl]methane (BIS-TRIS), Tris[hydroxymethyl]aminomethane (TRIZMA), and the like, and any mixture thereof.

The final chitosan-based liquid component has a pH above the pKa of chitosan (6.3-6.4), generally between 6.5 and 7.4, and a reduced content in acid. Typically, chitosan-glycerophosphate solutions at pH=7.0, prepared from chitosan, hydrochloric acid and disodium glycerophosphate, mainly contain water, chitosan-glycerophophate and NaCl.

All proposed liquid components have a pH ranging between 6.5 and 7.4, and an intrinsic viscosity ranging between 5 and 100,000 mPa·s at 21° C. All liquid components, being endothermally sensitive, have a sol-gel transition temperature, and form homogeneous solid aqueous gels at a temperature, between 15° C. and 60° C., preferably between 25° C. and 45° C., and more preferably at 35-40° C.

The liquid component may also comprise a certain amount of water-soluble salts such as phosphate salts or carbonate salts, or a mixture thereof. Typical salts are sodium phosphate or carbonate salts. This phosphate or carbonate salt concentration is generally ranging from 0 to 0.1 mole/l, generally below 0.05 mol/l.

Other organic compounds being nonbioactive may be admixed to the liquid component so as to provide specific chemical or physical properties. Representative compounds include polyols, sugar-polyols, saccharide-polyols and glycols, including glucose, fructose, maltose, saccharose, glycerol, mannitol, sorbitol, ethylene glycol oligomers, propylene glycol oligomers, and the like.

Incorporation of Bioactive Agents in the Liquid Component

Other ingredients can be incorporated to the liquid component to give specific biological actions to hard-tissues, either treating deficiencies or diseases, inducing or accelerating hard-tissue formation and repair, and the like. They are pharmaceuticals, chemicals, or biologically-active agents, or mixtures of agents, that can be totally or partially dissolved in the liquid component, or are water-insoluble artificial materials or living biologicals that can be dispersed in the liquid component. Those agents do not impair the endothermal sensitivity of the liquid component.

In one embodiment, the agents are inductive, protective or therapeutic agents, being water-soluble or partially water-soluble, and comprise osteoinductive agents such as growth factors, growth hormones, osteoinductive proteins and mixtures of osteoinductive proteins, genes and pharmaceuticals or drugs. Cytokines and growth factors (GF) may be selected typically from Epidermal GF, acidic Fibroblasts GF, basic Fibrosblast GF, Platelet-Derived GF AA, Platelet-Derived GF BB, Platelet-Derived GF AB and Tumour GF-beta. Osteoinductive agents may also be demineralized bone matrix, osteopontin, osteocalcin, sialoprotein, calcitonin, or a mixture thereof, or hard-tissue (bone) derived organic preparations, preferentially non-immunologic organic preparations.

Moreover, a suspension of living cells may be used to prepare the liquid component. Living cells may also adhered and be cultured onto the solid component such as on the calcium, fluoride, strontium, carbonate and phosphate salts under granular form. They also may be adhered and cultured on other solid materials that are added to the solid component (Ex: bioglass). They may also come from body's fluid or component such as the blood, bone marrow. Living cells may be selected among the cells that constitute the tissues or are precursors of the tissue cells.

Biological cell sources of bioactivity may be from allogeneous or preferably autogeneous tissue or fluid, such as cortical or cortico-cancellous bones, whole blood and blood components, bone marrow, cells isolated from tissues, stroma cells or hematopoietic cells, and the like.

Optionally, molecules being phophorylated amino acids or sequences of carbohydrate with phophorylated amino acids may be incorporated in the liquid component.

Bioactive agents can be incorporated at a soluble or non-soluble state. They can be complexed with other chemical molecules into a solid that is incorporated to the liquid component. They can be added to the liquid component as a non-soluble or sparingly soluble ingredient.

Representative biological additives to the liquid component are the patient's whole blood or blood components (autologous, soluble or non-soluble), the patient's bone marrow (autologous, soluble or non-soluble), the crunched patient's spongy bone (autologous, non-soluble), and antibiotics (gentamycin, vencomycin, tobramycin, etc).

Preparation of the Solid Component

The solid component comprises at least one of calcium, fluoride, strontium, carbonate and phosphate salts that are not easily soluble (sparingly or more likely insoluble) in aqueous media.

In the invention, the solid component is generally dry mineral powders or particles, or any mixtures of dry mineral powders or particles, also called "dry ingredients". It has a calcium composition, and preferably a calcium phosphate composition, having a good stability in aqueous environment at pH 6.5-7.4.

The size of the particles is not particularly crucial in the invention, although there exist preferred ranges of sizes to have optimal particle surface area, surface reactivity, biological reaction, dissolution rate, etc. Particle size, herein defined as an average particle size, may range from 0.1 microns to 1000 microns, preferably below 500-600 microns, and more preferably from 100 to 300 microns. Dry ingredients are sized and combined together by physico-mechanical milling/mixing techniques and instruments. This may be reached by a single milling/mixing and sieving step, or by a series of milling/mixing and sieving steps. The physico-mechanical mixing is not critical, may be operated with various techniques and instruments, but has to provide an intimate sizing and mixing of the dry ingredients.

Physico-mechanical milling/mixing techniques include mortar, or ball planetary mixing, and the like. A selection of the dry powder mixture may be operated following the dry milling/mixing, for example by sieving into an appropriate ingredient size. Shaker (rotary) mixing and ball mixing was preferentially used in the present invention. It is important that the dry ingredient milling/mixing is achieved without chemically altering the ingredient reactivity and without contamination. Mixing must be performed until occurrence of a uniform dry mixture. To ensure anhydrous conditions, the mixing of dry ingredients may be operated under strict anhydrous conditions (gas, environment control), or in anhydrous non-aqueous liquids, for example solvents such as hexane or absolute alcohols, all traces of water being preliminarily eliminated from this liquid. Identically, the dry mixture is preferentially stored under strict anhydrous conditions so as to avoid any contamination or cross-reaction with water. Solid additives, being organic or inorganic, may be admixed with the dry ingredients at the dry mixing step. Incorporation of bioactive agents in the solid component may be performed during the dry mixing, or later, during a second mixing step.

Sterilization of dry ingredient can be reached by current industrial sterilizing techniques such as gamma-irradiation at doses from 2.0 to 3.5 Mrad. Other sterilizing techniques and conditions can be performed such as high-temperature (>175° C.) or steam sterilization.

Self-Forming Hybrid Compositions/Bio-Materials: Preparation

In the present invention, self-forming hybrid compositions are prepared by first intimately mixing together the liquid component and the solid component. Mixing may be performed manually by kneading, or physico-mechanically by using homogenizers, mixers or mills, and the like. Alternatively, two syringes with or without a mixing tip are used to mix liquid and solid components of the composition. There is no special preference for the mixing instruments, but the composition must be homogeneous with as few agglomerations as possible, being a dispersion of the fine mineral particles of the solid component in the liquid component.

The liquid component is one selected among those previously described. One preferred basic liquid components comprise water, acid, chitosan and a soluble source of an organic mono-phosphate salt. Acid is generally selected among hydrochloric acid, phosphoric acid, acetic acid, lactic acid, and the like. The starting acidic aqueous medium is generally a 0.05 to 1N acid/water solution, and preferably a 0.05 to 0.5N solution. Chitosan is generally selected among partially N-deacetylated poly(glucosamine) having a deacetylation degree between 60 and 100%, preferably between 30 and 99% and more preferentially between 84 and 98%. Chitosan is present in the liquid component at a concentration ranging from 0.1% to 10% w/v, preferentially between 0.5 and 5.0% w/v, and more preferably between 0.5% and 3.0% w/v. The source of phosphate is generally an organic monophosphate dibasic salt, such as glycerol-2-phosphate and/or glycerol-3-phosphate sodium or magnesium salts, at a concentration between 0.1% and 20% w/v, and ideally between 1.0% and 10% w/v. The pH of said liquid component varies between 6.5 and 7.4, and preferably between 6.8 and 7.2. The viscosity of said liquid component is ranging between 5 mPa·s to 100,000 mPa·s, and preferably between 10 mPa·s and 1,000 mPa·s.

As previously described, additional reagents may be an organic mono-sulfonate salt and/or a second hydrophilic polymer, and/or an organic molecules, and/or a bioactive agent. The liquid component is preferably stored at cool temperatures, ideally between 0 and 4° C. Water-soluble salts such as carbonate or phosphate salts, or a mixture thereof, can be added to the liquid component, at concentrations below 0.1 mol/l.

The solid component is a solid mineral ingredient or a mixture of solid mineral ingredient that contains at least one of calcium, fluoride, strontium, carbonate and phosphate salts, and preferably at least one calcium phosphate. The calcium (phosphate) may consist in $Ca(H_2PO_4)_2.H_2O$ (MCPM), $CaHPO_4.2H_2O$ (DCPD), $CaHPO_4$ (DCPA), $CaZn_3(PO_4)_2$, $CaZnPO_4$, $CaNaPO_4$, $Ca_2PO_4Cl$, alpha-$Ca_3(PO_4)_2$ (alpha-TCP), beta-$Ca_3(PO_4)_2$ (beta-TCP), $Ca_3(PO_4)_2.H_2O$ (ACP), $Ca_4(PO_4)_2O$ (TTCP), $Ca_8H_2(PO_4)_6.5H_2O$ (OCP), $Ca_9(HPO_4)(PO_4)_5OH$ (CDA), $Ca_{10}(PO_4)_6(OH)_{2-2x}O_x$ (SHA), $Ca_{10}(PO_4)_6(OH)_2$ (PHA), and the like or derivatives thereof. The powder component is a calcium phosphate such as a hydroxyapatite [$Ca_{10}(PO_4)_6(OH)_2$], or a derived apatite (calcium deficient apatite, carbonated apatite, and the like), or a tricalcium phosphate [alpha-$Ca_3(PO_4)_2$ or beta-$Ca_3(PO_4)_2$], or an octacalcium phosphate [$Ca_8H_2(PO_4)_6.5H_2O$], or an amorphous calcium phosphate [$Ca_3(PO_4)_2.H_2O$], and the like, or a mixture thereof. Any carbonated and fluorinated, and strontium-containing calcium phosphates, as previously described, and the like or a mixture thereof, may be also used, including carbonated fluorinated strontium-containing, carbonated strontium-containing, fluorinated strontium-containing, and carbonated fluorinated calcium phosphates. Any amorphous form of the previously described calcium phosphates, and the like or a mixture thereof, may be incorporated as well.

Other mineral or inorganic solid component can be selected among non-phosphate calcium salts such as typically calcium sulfates, calcium titanates, calcium carbonates, calcium acetate, calcium glycerophosphate, calcium gluconate, and the like.

Other mineral may be added to the calcium compound of the solid component. Such other mineral can be Calcium, Strontium, Barium, Magnesium compounds, and the like, or titanate, sulfate, silicate compounds, and the like, or fluorinated, carbonated, strontied compounds, and the like, or a mixture thereof. Examples of such solid component composition may be a calcium phosphate with a sodium monofluorophosphate addition, or a apatite with a certain amount of a fluorinated or strontied apatite.

In a preferred embodiment, the solid component is preferentially 100% HAP $[Ca_{10}(PO_4)_6(OH)_2]$, or 100% TCP $[Ca_3(PO_4)_2]$, or 100% OCP $[Ca_8H_2(PO_4)_6.5H_2O]$, or a dry mixture of HAP, TCP and/or OCP. Typical dry mixture of the powder component is a HAP/TCP powder mixture (from 10:90 to 90:10). Preferentially, HAP/TCP contains the beta phase of TCP, but alpha phase can be used similarly.

The size of mineral solid varies between 0.1 and 1000 µm, generally between 20 and 300 µm, and is preferentially selected between 100 and 300 µm. For calcium phosphates, the calcium to phosphate ratio of the solid component varies from 1.0 to 2.0, and more generally from 1.3 to 1.7, and more preferentially from 1.5 to 1.7. The solid is a powder, a particulate, granules of any shape, or micro-spheres, and the like.

The solid component and the liquid component are intimately mixed together, with a liquid/solid (US) weight ratio between 0.05 g/mL and 2.0 g/mL, and preferentially between 0.1 g/mL and 1.2 g/mL, and more preferentially between 0.1 g/mL and 0.9 g/mL. The resulting ungelled slurry is injectable, and has a viscosity ranging between 5 and 1,000,000 mPa·s, and preferentially between 5 and 200,000 mPa·s. The hybrid composition can be partially gelled and remained injectable. Complete thermal gelling of such mineral-polymer composition does not exclude at all injectability and extrudability.

The liquid component is endothermally sensitive, and the resulting slurry is identically endothermally sensitive. This is shown by monitoring Theologically the viscoelastic parameters of the slurry, and more typically by monitoring the viscous and elastic moduli, and tan δ, of the liquid component and resulting slurry. Self-forming hybrid compositions are mainly self-gelling systems, with no self-hardening properties. The hybrid compositions form at 37° C. and 100% humidity a hybrid material that looks like a consistent gel-like material. The compression strength of resulting gel-like materials is low, typically below 1.0 MPa. This hybrid gel-like material can be remodeled in situ, and is resorbable as are its constitutive ingredients.

The resulting thermo-gelling slurry can be administrated to the body site:
  a) at an ungelled state, as a liquid, and it will gel in situ.
  b) at a partial gelled state, and it will end its gelling in situ.
  c) at a gelled state, being gelled in vitro, and it is delivered to the body site.

Mode of Administration—Application

The administration of the composition to hard-tissue defects, cavities, or any anatomical structures is performed percutaneously by injection through a catheter, cannula, trocar or needle of a gauge ranging from 7 to 27, preferably from 14 to 22, and more ideally from 16 to 22, and with the use of a syringe or any pressure injecting device, or by the use of endoscopic technique and instrument or during the course of an open surgical operation.

The compositions may be useful for medical and dental indications, in human or veterinarian procedures. They may be used in various known procedures such as:
  a) to favor and promote regeneration of bone lost due to local or systemic diseases, disorders or deficiencies (periodontal diseases, abscess, tumour resection, osteoporosis), to fill bone defects or cavities;
  b) to replace bone that is surgically removed or lost during a trauma;
  c) to favor and promote formation of bone in non-osseous sites, or in the vicinity of bone (intervertebral disks);
  d) to augment alveolar ridges, to fill extraction socket, to favor osteointegration of dental devices;
  e) to ensure retention and strength in situ of other orthopaedic devices (pin, prosthesis, fixation);
  f) to ensure percutaneous delivery of therapeutic agents to tissues (drug delivery);
  g) to favor the anchorage and interface between bone and articular cartilage; and
  h) to repair the reconstruction, repair and function recovery of musculo-skeletal tissues such as bones, cartilages and fibrocartilages.

More generally, the compositions may be useful for all repair, regeneration, filling, replacement procedures associated to hard-tissues as well as for delivering drugs or bioactive agents to hard-tissues. It can also be administered to soft-tissues such as cartilages and fibrocartilages.

The composition can be mixed with patient's blood or bone marrow or crunched spongy bone prior to injection on the site. This addition increases the osteogenic potential of the composition and bio-material.

The composition can be injected for filling and repairing internal bone cavity, for local treatment of osteoporotic bones, for demineralized bones and bone demineralization disorders; for bone defects or cavities, for example in the case of periodontal defects with bone loss, augmentation of the alveolar ridge or surgically-performed hard-tissue defects following resection of diseased hard-tissue parts; for bone fractures for delivering agents that accelerate the sequence of fracture healing; as well as for bone fusion, such as vertebral bone fusion.

Typical applications of the self-forming mineral-polymer hybrid composition consists in solitary bone lesions such as those observed with osteomyelitis, round cell lesions, fibrous displasia, bone cyst, chondromyxioid fibroma, osteosarcoma, non-ossifying sarcoma, endochondroma, chondroblastoma, joint revision osteolysis, or the like.

In another application, the mineral-polymer composition is applied at the interface with a prosthesis or an implant (orthopaedic) such as a prosthetic joint (hip, knee) or a screw (pedicular). It can be used for joint revisions.

Another application is the treatment of metaphyseal and diaphyseal fractures in association with a fixation device. Said mineral-polymer composition can be associated with osteoinductives such as autologous blood or bone marrow, growth factors, etc to accelerate the phase sequence of fracture/bone healing.

The present invention will be more readily understood by referring to the following examples which are given to illustrate the invention rather than to limit its scope.

Example I

Preparation of Liquid Component

The liquid component of bone composition is an endothermally self-forming aqueous solution comprising one hydrophilic cationic polymer and one water-soluble organic monophosphate source. A representative liquid component is a chitosan/glycero-phosphate [chitosan-GP] aqueous solution. An acidic chitosan aqueous solution (2.0% w/v) was made with a chitosan previously deacetylated at 83-97%, filtered and dialyzed, and was prepared from a 0.097M (0.10M) HCl solution. A chitosan/glycerophosphate aqueous solution was prepared from the 2.0% (w/v) chitosan in HCl aqueous solution and a 54% (w/v) disodium glycerophosphate in distilled water solution. Final concentrations (w/v) in the self-gelling chitosan/glycerophosphate systems was approximately 1.6-2.0% (chitosan) and 6.75-8.2% (glycerol-phosphate) (see Table 1).

TABLE 1

Buffering/thermo-gelling agents for liquid components having 1.0-2.0% by weight of chitosan.

| Buffering/<br>Thermo-gelling<br>agents | Example<br>contents<br>(% w/v) | Remarks |
|---|---|---|
| Glycero-phosphate salts | 4-10 | |
| Glucose-phosphate salts | 6-12 | |
| Fructose-phosphate salts | 1-6 | |
| Histidine | 2-10 | Histidine and glucosamine used |
| Glucosamine | 2-10 | as co-buffering agent with glycero-phosphate. |
| BIS-TRIS | 1-8 | Used alone or mixed with glycero-phosphate. |
| MES (sulfonate) salt | 1-4 | Used alone or mixed with glycero-phosphate. |
| HEPES (sulfonate) salt | 1-4 | Used alone or mixed with glycero-phosphate. |
| TES (sulfonate) salt | 1-4 | Used alone or mixed with glycero-phosphate. |

Glycerophosphate (GP) salts act herein as buffering/thermo-gelling agents for the chitosan solution. Other buffering/thermo-gelling phosphate sources may be used, typically organic monobasic phosphate salts, such as glucose-phosphate or fructose-phosphate salts. Other buffering agents may be also associated with glycerophosphate salts so as to enhance the buffering/thermo-gelling action such as amino acids or organic sulfonate salts. Table 1 summarizes the potent composition of liquid components. Histidine was typically admixed with GP in the chitosan solution (Ex: 1.5% w/v chitosan, 4.0% w/v GP+4.0% w/v histidine). BIS-TRIS may be used alone as a buffering/thermo-gelling agent (Ex: 1.5% w/v chitosan+2.0% w/v BIS-TRIS). HEPES, TES or MES sulfonate agent may be used alone as a buffering/thermo-gelling agent (Ex: 1.5% w/v chitosan+2.0% w/v HEPES, TES or MES).

a) Addition of a Second Water-Soluble Polymer in the Liquid Component

Figure 6A:
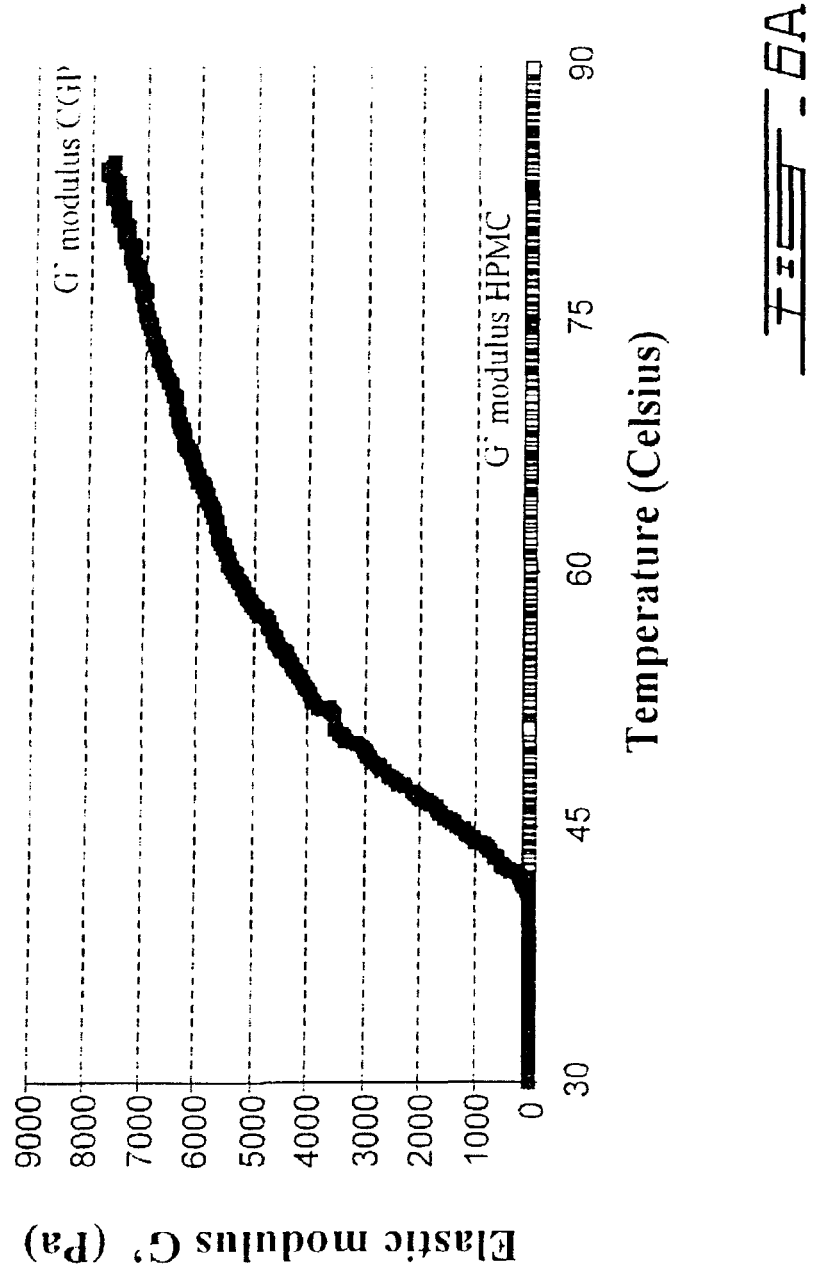
FIG. 6 illustrates the thermo-gelling the elastic modulus with the temperature (FIG. 6A) and the phase angle with the temperature (FIG. 6B) between two different liquid component, the chitosan-glycerophosphate system that spontaneously gels around 40° C., and the hydroxypropyl methylcellulose (HPMC) system that gels around 60° C., the chitosan-glycerophosphate systems gel stronger that HPMC ones.
Figure 6B:
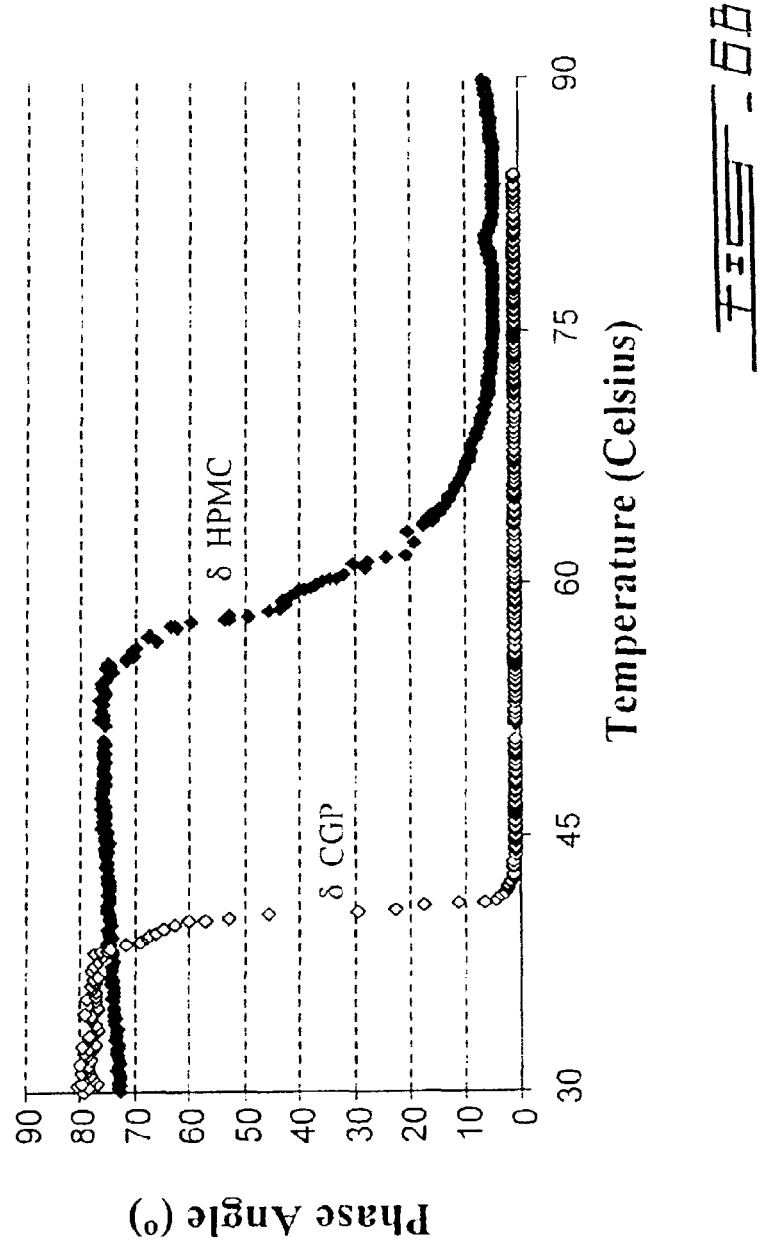
Figure 8:
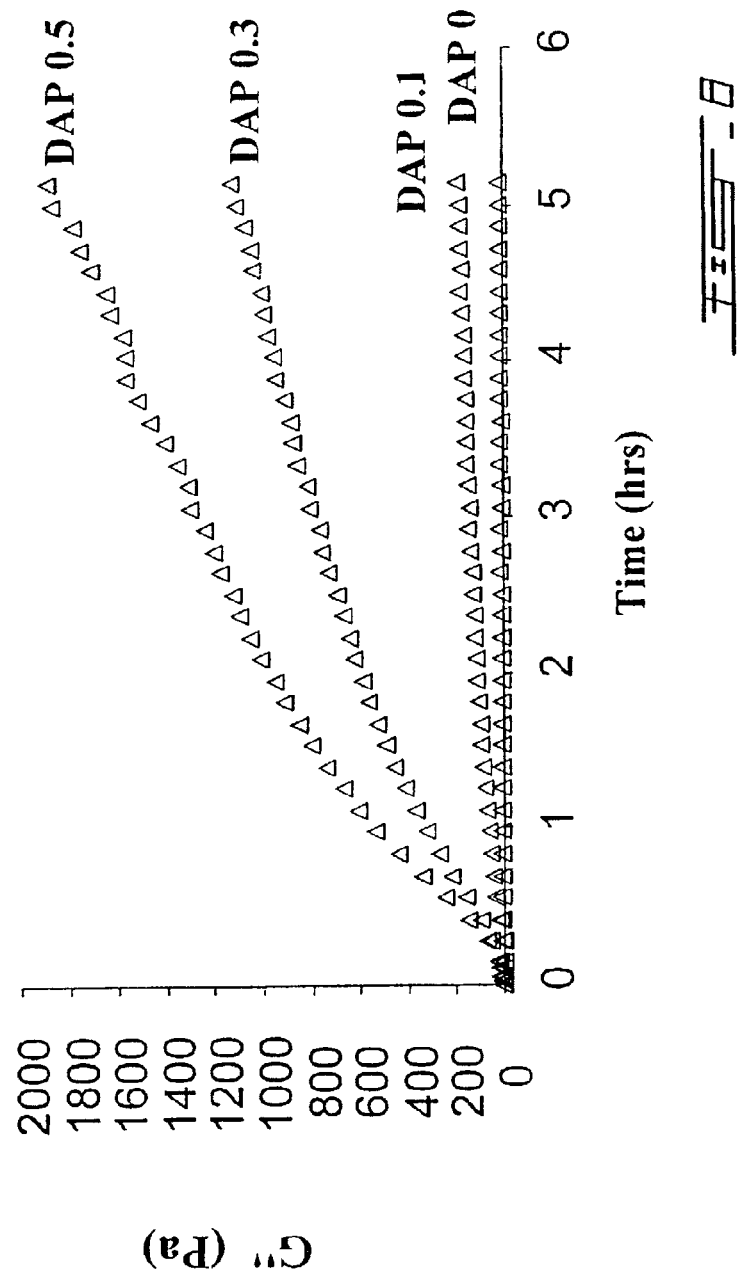
FIG. 8 illustrates the rheological characteristics of DAP-CGP hybrid systems (chitosan 2% w/v; GP 8.2% w/v), the viscous modulus (G") is given during the gelling (37° C.)

A second water-soluble polymer may be dissolved in the chitosan-GP aqueous solution. Table 2 gives the composition of liquid component consisting in chitosan-GP plus a water-soluble polymer. Glycerophosphate may be added prior to the dissolution of the second polymer, or after the dissolution of the second polymer. Thermosensitive polymers such as the methyl cellulose, hydroxypropyl methylcellulose or Pluronic® were found to be the more sensitive to the concentration in glycerophosphate salts. Those salts were found to affect the gelling or precipitating temperature of the polymer, thus leading to a precipitation of the chitosan/GP/polymer (2) system (FIG. 6).

All polymers (2) were dissolved in a prepared chitosan-GP solution, except for collagen, and more generally other polycationics, that are dissolved in combination with the chitosan.

TABLE 2

Liquid component compositions having an admixed second water-soluble polymer.

| Polymer (2) | Polymer<br>content<br>(w/v) | Chitosan<br>content<br>(w/v) | GP<br>content<br>(w/v) | Remarks |
|---|---|---|---|---|
| Hydroxyethyl Cellulose | 1.0% | 2.0% | 8.0% | Form gels. |
| Hydroxypropyl Methyl Cellulose | 0.55% | 1.0% | 4.5% | Form gels. |
| Polyethylene glycol | 1.0% | 2.0% | 8.0% | Form gels. |
| Methyl Cellulose | 1.0-2.0% | 1.0-2.0% | 4.0-6.0% | Form gels. Precipitation may occur with higher GP contents. |
| Pluronic ® | 1.0% | 2.0% | 2.0% | Form gels. Precipitation may occur with higher GP contents. |
| Collagen (type I) | 1.0% | 1.0% | 8.0% | Form gels. |

All presented concentrations (%, mol/l) are final.

b) Addition of Water-Soluble Ingredients of Interest

Some organic molecules that are soluble or miscible with water may be added to the chitosan-based liquid component to give modified or improved physico-chemical characteristics, mechanical or handling performances, or biological properties. This includes without limitation polyols, sugars, amino-acids, saccharides, and polysaccharides.

Polyols & Sugars

Of particular interest may be the polyols such as polyols having diol hydrocarbon moieties which may be useful for the processing or the performances of the liquid component (see Table 3). Among those polyols, sugar-polyols, saccharide-polyols and glycols are preferred: glycerol, mannitol, sorbitol and ethylene glycol compounds such as the triethylene glycol, tetraethylene glycol were found to be good representative examples, being attractive and bringing modifications or improvements to the liquid component or resulting thermo-formed gel. Sugars such as fructose, glucose, etc may be used similarly.

TABLE 3

Liquid component compositions having added water-soluble non-polymeric ingredient (Polyols)

| Polymer (2) | Ingredient content (w/v) | Chitosan content (w/v) | GP content (w/v) | Remarks |
|---|---|---|---|---|
| Glycerol | 0.1-1.0 | 2.0% | 8.0% | Form gels. Changed rheological parameters of gels. Stabilize chitosan sol viscosity. |
| Sorbitol (Mannitol) | 0.1-1.0 | 1.0% | 4.0% | Form gels. Changed rheological parameters of nonsterile gels. Stabilize chitosan sol viscosity. |
| Ethylene glycol | 0.1-1.0 | 2.0% | 8.0% | Form gels. Changed rheological parameters of nonsterile gels. Stabilize chitosan sol viscosity. |
| Tri-(Tetra-) Ethylene glycol | 0.1-1.0 | 2.0% | 8.0% | Form gels. Changed rheological parameters of gels. Stabilize chitosan sol viscosity. |

All presented concentrations (%, mol/l) are final.
Polysaccharides (GAGs)

Other water-soluble (bio)chemical ingredients may be of interest to be added to the chitosan-GP liquid component. However, such ingredients must not disturb the chitosan-GP composition (ingredient) and its thermo-gelling property. Glycoaminoglycans may be added to the chitosan-GP solution to a certain extent. It must be taken care of not inducing precipitation of chitosan. In Table 4, heparin was used as the GAGs to be added. Chitosan solutions were 4.0% w/v chitosan (deacetylation 95%) in 0.19M HCl. GP solutions were 54.6% w/v in water. Heparin in water solutions were at 1 mg/mL (A), 0.1 mg/mL (B), 10 μg/mL (C) and 1 μg/mL (D).

TABLE 4

Liquid component compositions having added water-soluble non-polymeric ingredient (Heparin)

| # | Composition | pH | Remarks |
|---|---|---|---|
| 1. | 500 μL chitosan + 150 μL GP 250 μL water + 100 μL Heparin (B) | 7.04 | Gels. |
| 2. | 500 μL chitosan + 250 μL water 150 μL GP + 100 μL Heparin (C) | 7.01 | Gels. |
| 3. | 500 μL chitosan + 250 μL water 150 μL GP + 100 μL Heparin (B) | 6.87 | Gels. |
| 4. | 500 μL chitosan + 250 μL water 150 μL GP + 100 μL Heparin (A) | 6.97 | Reduced precipitation. Gels. | c) Addition of a Second Water-Soluble Phosphate Source to the Liquid Component

An acidic chitosan aqueous solution (2.0-4.0 w/v) was made with a chitosan deacetylated at 83-85%, filtered and dialyzed, and was prepared from a 0.1M HCl solution.

A chitosan-GP aqueous solution was prepared from a pre-cooled (4° C.) chitosan in HCl solution and a 54-55% (w/v) disodium glycerophosphate (GP) in distilled water solution. The pH of the resulting liquid chitosan-GP solution was measured at 21° C. A phosphate solution (1) was prepared with 0.144 g/l $KH_2PO_4 \cdot 7H_2O$ potassium dihydrogen phosphate hydrated) and 0.795 g/l $Na_2HPO_4$ disodium hydrogen phosphate) and had a pH of 7.4 at 20° C. Amounts of the chitosan-GP solution and phosphate solution (1) were admixed homogeneously, then the pH of the resulting solutions was measured. The solutions were finally disposed at 37° C. for gelation, all signs of precipitation being noted. In Table 5, all chitosan-GP+phosphate solution (1) (80:20 to 50:50, vol) showed no signs of precipitation, and gelled within 30 minutes at 37° C.

TABLE 5

Composition of liquid components supplemented with a second source of water-soluble phosphate.

| Composition | pH | Chitosan:GP (% w/v) | [Phosphate] mol/l | Gelling time (initial) | Precipitation |
|---|---|---|---|---|---|
| 10 ml chitosan-GP | 7.0 | 2.0:8.2 | 0 | 30 minutes | No |
| 8 ml chitosan-GP + 2 ml phosphate (1) | 6.9 | 1.6:6.6 | 0.0014 | 30 minutes | No |
| 7 ml chitosan-GP + 3 ml phosphate (1) | 6.9 | 1.4:5.7 | 0.0021 | 30 minutes | No |
| 5 ml chitosan-GP + 5 ml phosphate (1) | 6.9 | 1.0:4.1 | 0.0035 | 30 minutes | No |
| 8 ml chitosan-GP + 2 ml phosphate (2) 1:1 | 6.9 | 1.6:6.6 | 0.04 | Slow gelation | No |
| 7 ml chitosan-GP + 3 ml phosphate (2) 1:1 | 6.9 | 1.4:5.7 | 0.06 | Slow gelation | No |
| 5 ml chitosan-GP + 5 ml phosphate (2) 1:100 | 6.95 | 1.0:4.1 | 0.001 | 30-40 minutes | No precipitation |

All presented concentrations (%, mol/l) are final.

A concentrated phosphate solution (2) was prepared from 283.92 g/l of $Na_2HPO_4$ (0.2 mol/l disodium hydrogen phosphate) and 239.96 g/l of $NaH_2PO_4$ (0.2 mol/l sodium dihydrogen phosphate) and had a pH of 7.4 at 37° C. This phosphate solution was used with dilutions at 1:1, 1:10, 1:100 and 1:1000. Equal volumes (50:50) of the diluted to concentrated phosphate solution (2) and chitosan-GP solution were mixed homogeneously. The pH of the resulting solutions was measured, and the solutions disposed at 37° C. for gelation, all signs of precipitation being noted. All chitosan-GP/phosphate (2) gelled with various rates at 37° C.

A more concentrated phosphate solution (3) was prepared: 0.5 mol/l $NaH_2PO_4$ (600 g/l) and 0.5 mol/l $Na_2HPO_4$ (709.8 g/l). Volumes of the concentrated phosphate solution (3) was added to chitosan-GP solutions, and mixed homogeneously. In Table 6, the pH of the resulting solutions was measured, and the solutions disposed at 37° C. for gelation, all signs of precipitation being noted. Chitosan-GP is fully compatible with 5 mM PBS solution at pH 7.2-7.4. Compatibility depends upon the phosphate content (Tables 1a-1b): the addition of highly concentrated phosphate solutions (especially dibasic phosphates) renders the chitosan-GP system more turbid and prone to precipitation or heterogenous gelation.

TABLE 6

Composition of liquid components supplemented with a second source of water-soluble phosphate.

| Composition | pH | Chitosan:GP (% w/v) | [Phosphate] mol/l | Gelling time (initial) | Precipitation |
|---|---|---|---|---|---|
| 10 ml chitosan-GP | 7.0 | 4.0:8.2 | 0 | 30 minutes | No |
| 9 ml chitosan-GP + 1 ml phosphate (3) | 6.7 | 3.6:7.4 | 0.05 | | More turbid |
| 8 ml chitosan-GP + 2 ml phosphate (3) | 6.7 | 3.2:6.6 | 0.1 | | Highly turbid; Gels heterogeneously | d) Addition of a Water-Soluble Carbonate Source to the Liquid Component

The chitosan-GP solutions were prepared as in Example 1c.

A carbonate solution was prepared from a 0.2 mol/l solution of monosodium carbonate, having a pH of 8.16 at 21° C. Equal volumes (50:50) of the diluted (1/10) to concentrated carbonate solution and chitosan-GP solution were mixed homogeneously. A carbonate (0.1 mol/l)+phosphate (0.1 mol/l) solution was also used. The pH was measured, and the solutions were disposed at 37° C. for gelation, all signs of precipitation being noted (see Table 7). Chitosan-GP systems are fully compatible with carbonate buffer such as a 5 mM phosphate/carbonate buffer at a pH of 8.8. But, this compatibility will decline for too high carbonate contents.

TABLE 7

Composition of liquid components supplemented with a source of water-soluble carbonate.

| Composition | pH | [Carbonate] mol/l | Gelling time (initial) | Precipitation/ Remarks |
|---|---|---|---|---|
| 10 ml chitosan-GP | 7.0 | 0 | 30 minutes | No |
| 8 ml chitosan-GP + 2 ml carbonate | 7.0 | 0.04 | 30 minutes | No |
| 6 ml chitosan-GP + 4 ml carbonate | 7.1 | 0.08 | 30 minutes | No. Some sparse complexes may occur by the surface. |
| 5 ml chitosan-GP + 5 ml carbonate | 7.1 | 0.10 | 30 minutes | No. Fibrous complexes occur sparsely at the upper level. |
| 5 ml chitosan-GP + 5 ml carbonate 1:10 | 6.95 | 0.01 | 30 minutes | No |

All presented concentrations (%, mol/l . . . ) are final.

In Example 1d, liquid chitosan-GP formulations supplemented with water-soluble phosphates and/or carbonates present a reduced shell-life and stability, even at low temperatures (4° C.). This is dose-dependent, the more concentrated is the content of water-soluble phosphate and/or carbonate in the chitosan-GP formulation, the less stable is the resulting solution.

e) Typical Preparation of Sterile Liquid Component

Sterilization Method of Liquid Components

Sterilization of liquid component can be performed during the preparation and processing of the chitosan-GP solutions. The chitosan-GP systems can not be sterilized by energizing methods, due to unexpected and undesirable thermal gelling. Chitosan solutions (no GP) and GP solutions (no chitosan) are to be sterilized separately. GP aqueous solutions have no viscosity and are sterilized by filtration in all cases, without any noticeable adverse effects. Chitosan materials (solid) or chitosan solutions (acidic aqueous medium) must be sterilized while avoiding the occurrence of significant degradative effects on both chitosan polymer and chitosan-GP systems.

The preferred methods of sterilization of chitosan comprises autoclaving chitosan powder or solution, and gamma-irradiation of nonliquid chitosan material (including frozen solution)(see Table 8).

TABLE 8

Effects of sterilizing on Chitosan-GP systems (no additive)

| Chitosan sterilization | Effects an chitosan biopolymer | Effect of thermo-gelling Chitosan-GP systems. |
|---|---|---|
| Autoclaving of chitosan solutions in acidic media. | Controlled modification; | Gels (slightly decreased gelling rate). |

TABLE 8-continued

Effects of sterilizing on Chitosan-GP systems (no additive)

| Chitosan sterilization | Effects an chitosan biopolymer | Effect of thermo-gelling Chitosan-GP systems. |
|---|---|---|
| Autoclaving of chitosan suspension in water. | Controlled modification; | Modify gel properties. |
| Irradiation of chitosan materials (4° C.). | Controlled modification; | Gels (slightly decreased gelling rate). |
| Irradiation of chitosan materials (20° C.). | Stronger modification; | Gels (affect the gelling rate). |
| Irradiation of chitosan solutions (−80° C.). | No to nonsignificant modification; | Gels (no changes). |

Example II

Incorporation of Bone Healing and/or Inductive Agents into the Liquid Component a) Incorporation and Compatibility of Whole Blood and Bone Marrow in the Liquid of Mineral-Polymer Composites.

Blood component or whole blood from patient to be treated is often used to mix with bone filling materials (Ex: calcium phosphate or carbonate granules mixed with autologous blood).

Figure 17:
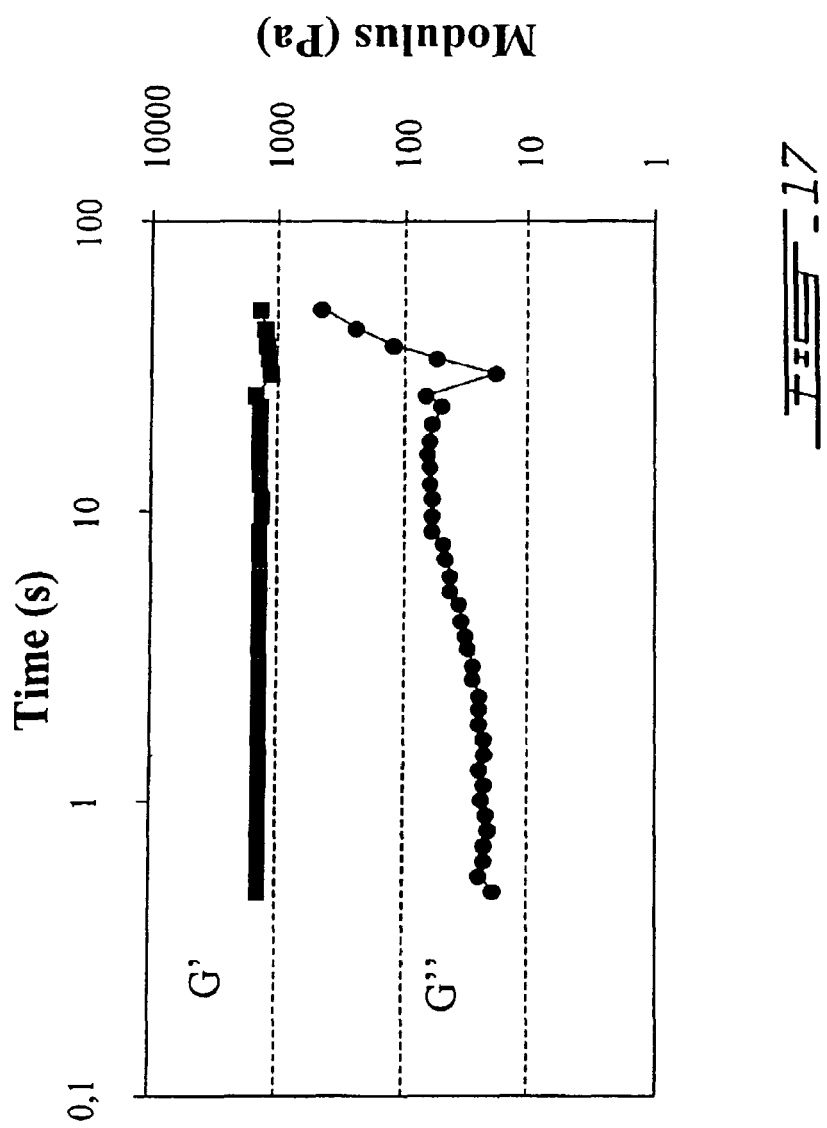
FIG. 17 illustrates the gel stability expressed by the modulus G' and G" versus the frequency, demonstrating gel formation of chitosan-glycerophosphate system mixed with rabbit whole blood (blood content: 15% v/v), the gelling being controlled rheologically at 37° C.

A fresh blood sample was collected from auricular arteries and from subchondral defects of rabbits. Blood was admixed with the liquid component of the mineral-polymer composites (chitosan-GP). Bone marrow was collected in rabbit from tibia and femur, and used fresh. Upon complete and rapid homogenization, the gelling of this blood containing liquid component was monitored at 37° C. by rheological analyses (FIG. 17). The gel has an elastic modulus (G') about 800-1000 Pa after 9 hrs at 37° C.

This demonstrated that the thermo-gelling of the liquid component is not affected by blood or marrow and enables to incorporate blood and its components, and bone marrow, within the thermo-gelling hybrid formulation.

b) Incorporation and Release of Proteins (Albumin) in the Liquid and/or Solid Component of Mineral-Polymer Composites Bovine serum albumin (BSA) was the protein used to model the protein incorporation and release from hybrid formulations, either by the liquid and/or solid component.

Incorporation of BSA in the liquid component was performed by incorporating directly the BSA to the liquid component formulation. Using a 2-syringe procedure, a chitosan solution and a glycerophosphate solution are admixed homogeneously, then the chitosan-GP solution is similarly admixed with a BSA in PBS (×1) solution. The final chitosan content in these gels were 1.44, 1.8 and 2.16% w/v. The final BSA content in these gels was 250 µg/ml. Gels are molded in petri dishes (constant surface area) (37° C., 1 h), then covered with 10 ml of PBS (×1). At the desired time, a 1000 µl solution specimen is collected for titrating the BSA content, and replaced by 1000 µl of fresh PBS solution. The BSA content is determined spectrophotometrically by using a Coomassie Plus Protein assay (Pierce). The BSA released from the chitosan-GP gels is determined at 1, 3, 6, 24, 48 h, 4, 6 days, etc. The BSA release from chitosan-GP gels is rapid, and by 24 hrs, at least 50% of the BSA is totally released from the gels. Incorporation of BSA in the solid component was performed by contacting Biphasic Calcium Phosphate granules (2 sizes: <150 µm, 150-250 µm) with Bovine Serum Albumin (BSA) solutions. The BCP/BSA weight ratio was 50 mg of BCP for 500, 1000 or 2500 µg of BSA. Initial BSA solutions were prepared in Phosphate Buffered Solution (PBS ×1) at BSA concentrations about 1, 2 or 5 mg/ml. A 500 µl of BSA solution was poured onto 50 mg of the BCP granules. Adsorptions were performed in centrifugation filters (Nanosep MF Microconcentrator) with a filter size of 0.45 µm. Adsorption was done at 37° C. for 24 hrs. Following adsorption, BCP granules were collected by ultracentrifugation for 10 minutes at 13000 rpm. The remaining BSA solution is collected. BCP granules were disposed in cell culture inserts (0.4 µm filter) of a 24-well plate, and covered with 1.5 ml of PBS (×1). At the desired time, a 500 µl solution specimen is collected for titrating the BSA content, and replaced by 500 µl of fresh PBS solution. The BSA content is determined spectrophotometrically by using a Coomassie Plus Protein assay (Pierce). The BSA released from the BCP granules is determined at 1, 3, 6, 24, 48 h, 4, 6 days, etc. The BSA release from BCP granules is progressive.

The BSA releases are equivalent for both sizes, and correspond to a total release about 40 micrograms after 700 hours (20 micrograms after 200 hours).

c) Incorporation and Release of Bone Proteins (BP) in the Liquid Component of Mineral-Polymer Composite.

The osteogenic agent was a bone protein (BP), in fact a pool of bone morphogeneic proteins that were solubilized in an acidic aqueous environment. The chitosan-GP aqueous solution was prepared as described in Example 1. A BP solution was made by dissolving the proteins in a 0.01M HCl (6.0 mg/ml). Three volumes of the BP solution were sampled, and carefully admixed to chitosan-GP solutions to give clear homogeneous chitosan-GP+BP compositions having distinct contents in proteins. The volume of all prepared compositions was completed with sterile water to 12.5 ml as required. All operations were performed at 4° C. under sterile conditions. The final BP content of the three compositions was 33, 100 and 330 µg/ml. Gel formation of all BP containing compositions was reached within few minutes at 37° C. The incorporation of BPs did not interfer with the gel formation. Gelled chitosan-GP/BP samples were tested in vitro by activity/release assays, and evaluated in vivo by a rodent subcutaneous assay. A rodent subcutaneous assay was used: Long-Evans rats (20) were anesthetized with sodium pentobarbital (400 µg). Gel-containing samples (200 µl) were injected subcutaneously in the absence of an incision. The gel formed a sphere structure. Each group contained 5 animals. The gel compositions were compared using variable BP doses (0, 10, 30 µg). The in vivo subcutaneous assay demonstrates that the BP is active in the chitosan-GP formulation, thus leading to induction of bone and cartilage neo-tissues.

Bone healing factors that are useful for fracture healing were selected as representative bone healing agents to be incorporated into the liquid component.

c) Incorporation and Release of Fibroblast Growth Factor (FGF) in the Liquid Component of Mineral-Polymer Composite Fibroblast growth factor (basic, bFGF) was used here as a Growth Factor member of the TGF-□ GF family to be incorporated in the liquid component and hybrid materials. bFGF and bFGF with Heparin were added to the chitosan-GP solutions, bFGF and bFGF/Heparin alone being used as controls. Heparin in the chitosan-GP solution was used at 10 µg/mL while bFGF was at 1 µg/mL. Chitosan-GP (1 mL) solutions were disposed in dishes, with PBS and 50 µg/mL bovine serum albumin, at 37° C. A 1 mL of the medium was collected at 0, 6, 24, 48, and 72 hours. The bFGF is quantified by ELISA (Quantikine FGF basic immunoassay). The bFGF in Chitosan-GP gels (no heparin) is mainly released by 24 hrs. When incubated with heparin, bFGF (+heparin) remained within chitosan-GP gels, and the release is clearly slowed down.

Additionally to the liquid component, bFGF and other GFs can be immobilized by the way of the solid component, or incorporated directly in the hybrid compositions.

d) Incorporation of Human Demineralized Bone Powder (HDBP) to the Mineral-Polymer Composite.

Demineralized bone powder (DBP) is a demineralized bone matrix (DBM) material transformed into solid powder, and is composed of the non-mineral non-living organic bone components (collagen, bone proteins . . . ). Demineralized bone matrix is osteoinductive. A cortical demineralized bone powder (CDBP) (Community Tissue Services, OH & Impladent, NY, USA) from human allografts was selected for typical examples. It is an allogenic cortical demineralized bone matrix that has been crushed in particles about 0.3-0.5 mm in size. CDBP was sterilized by irradiation and freeze-dried. As for allografts, CDBP was tested negative for HBsAG, anti-HBc, anti-HCV, STS, HIV 1/2, HTLV-I and HIV-1 antigen. A chitosan-GP formulation basis was obtained first by preparing a 2.3% w/v chitosan (84% deacetylation) in 0.10M HCl solution, and then by admixing the desired amount of a 55% w/v disodium glycerophosphate in distilled water solution. Final concentrations in the clear liquid chitosan-GP formulation were around 1.8-2.0% w/v chitosan and 8.0% w/v glycerophosphate.

CDBP was incorporated in a solid state to the chitosan-GP solution, thus resulting in a CDBP in chitosan-GP suspension. Loading of chitosan-GP with CDBP (Impladent Ltd., NY, USA) was determined by initial solid to liquid weight or volume ratio. The chitosan-GP/CDBP compositions were gelled at 37° C., entrapping homogeneously the CDBP.

Example III

Self-Forming Hybrid Composition and Material

Different calcium phosphate materials were used to form self-forming (gelling) hybrid compositions and materials (FIG. 1). All selected calcium phosphates were recognized (clinically) as being osteoconductive. Table 9 gives the corresponding compositions and S/L ratios.

mined by solid to liquid weight ratio, e.g. 1:10, 3:10 & 5:10 S/L loading ratio. Typical experiments were conducted with a 3:10 Ca—P loading (Table 9).

Durapatite particles were selected by sieving in 0-125 μm diameter, 212-250 μm diameter and >250 μm diameter size groups. Homogeneous mixing of Ca—P ceramics in chitosan-GP was achieved by manual kneading and magnetic stirring during 2-3 hours. The resulting slurries generally show greater extrudability or flowing properties which is observed by the viscosimetric analysis. It shows that higher shear rates result in lowering the viscosity (<10,000 mPa·s), the higher viscosity being observed at low shear rates (up to 60,000 mPa·s).

All hybrid compositions rheologically demonstrate a self-gelling behaviour that is typical of the liquid component property. In nearly all cases, the Durapatite loading induces more elevated viscoelastic parameters such as typically the elastic and viscous moduli (G' and G"). Durapatite (212-250 μm) incorporation seems to be the most efficient in improving G' and G". To some extent, the G' and G" increasing rates seems to be linerally correlated with the S/L ratio. Mechanical performances expressed by compression modulus (transient and equilibrium) are not markedly enhanced by the Durapatite incorporation although 3/10 to 5/10 loading seemed to provide hybrid gels with higher compressive strengths (FIGS. 2, 4, 5, 7, 8, and 12).

b) Hybrid Materials with Tricalcium Phosphate (TCP)

Figure 3:
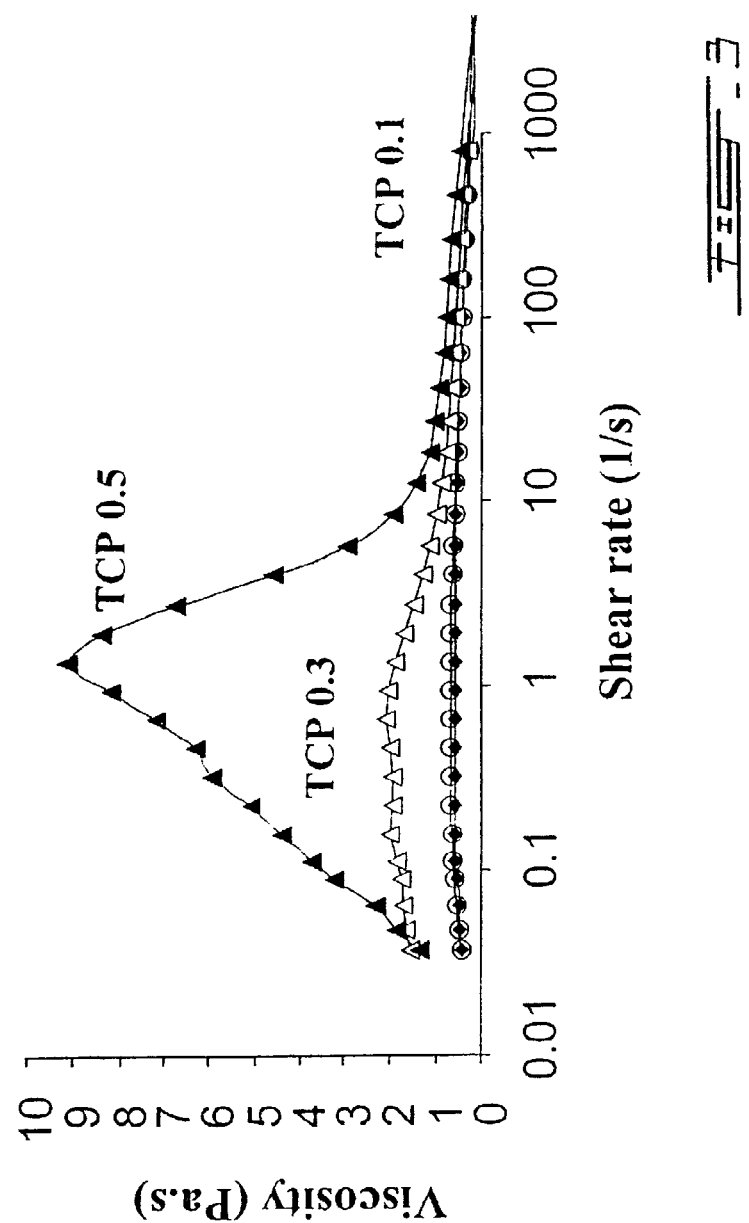
FIG. 3 illustrates the viscosity of TCP-CGP hybrid systems (chitosan 2% w/v; GP 8.2% w/v) as a function of the shear rate (20° C.)
Figure 4:
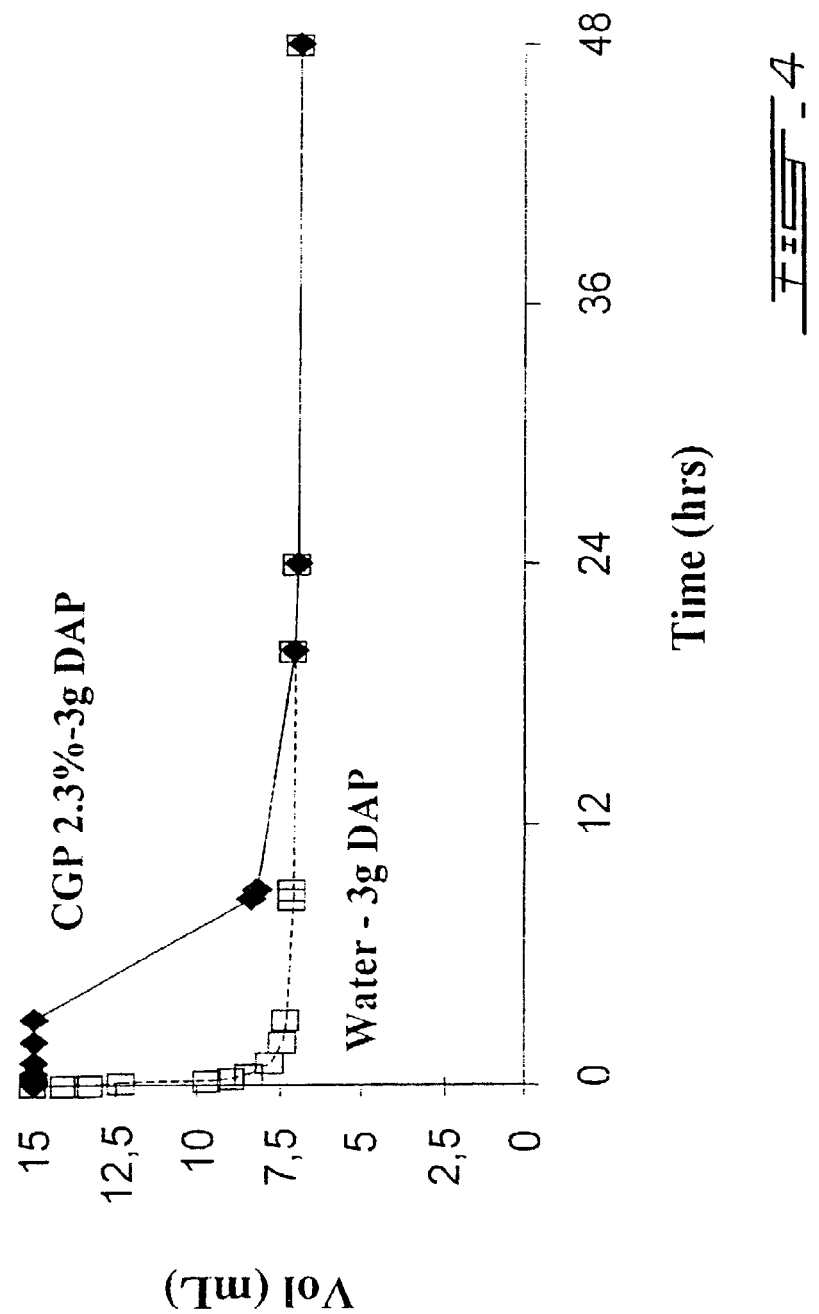
FIG. 4 illustrates the sedimentation tendency of DAP particles in a CGP solution and water wherein CGP was 2.3% w/v chitosan and DAP load was 3 g.
Figure 5:
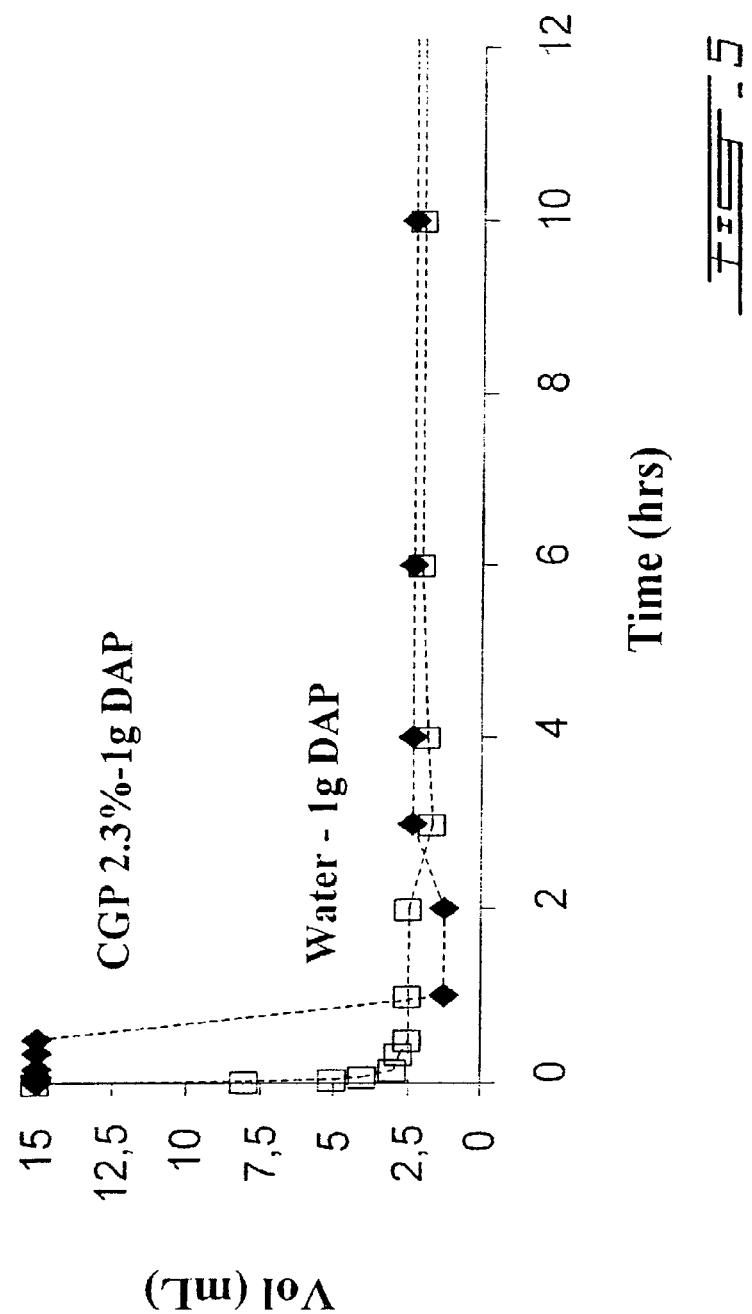
FIG. 5 illustrates the sedimentation tendency of DAP particles in a CGP solution and water wherein CGP was 2.3% w/v chitosan and DAP load was 1 g.
Figure 9:
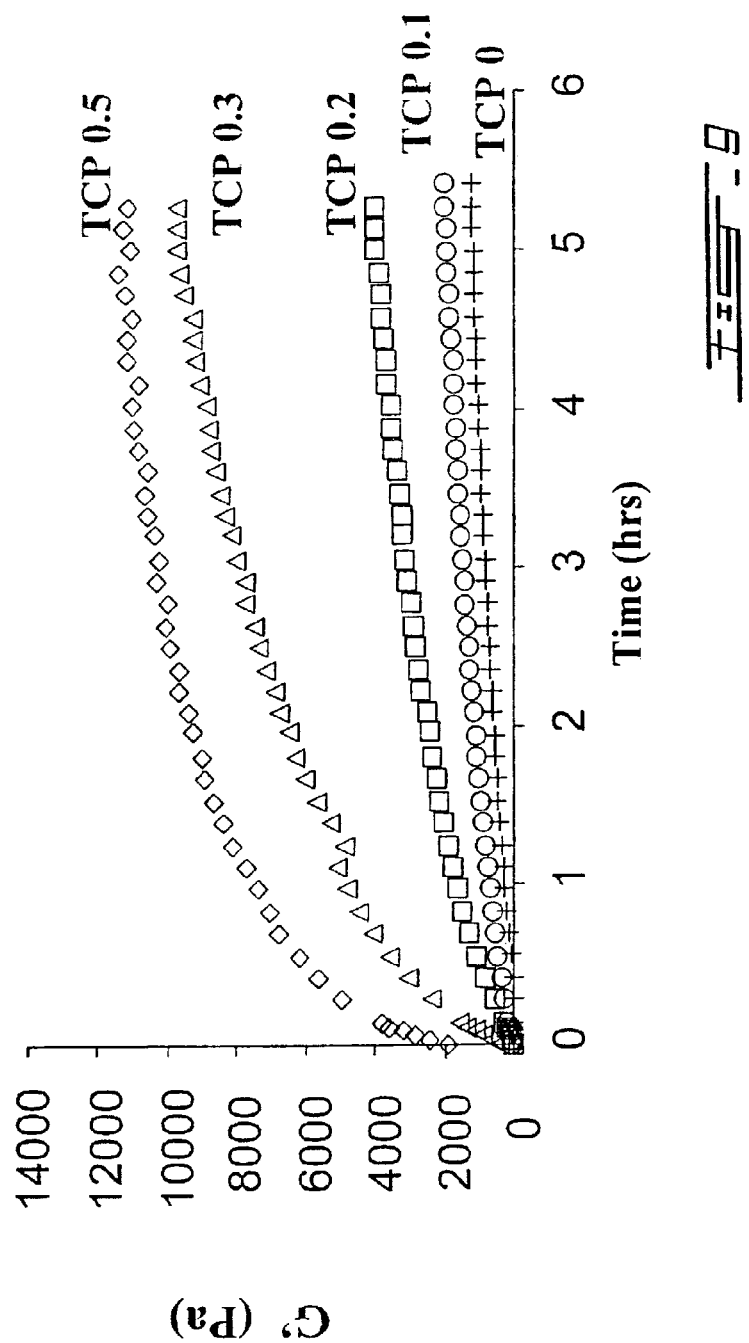
FIG. 9 illustrates the evolution of the G' modulus of CGP systems loaded with TCP (chitosan 2% w/v; GP 8.2% w/v) for a gelling at 37° C.

The selected chitosan-GP solution was the same as previously described in Example 3a above. Loading in tricalcium phosphate (TCP) particles as determined by solid to liquid weight ratio varied, (1:10, 3:10 & 5:10 S/L). Typical experiments were conducted with a 3:10 Ca—P loading (Table 9). All chitosan-GP/TCP compositions were monitored by viscosimetric and rheologic methods, and formed solid hybrid gels at 37° C. (FIGS. 3 and 9).

c) Hybrid Materials with Synthetic Nonceramic Hydroxyapatite (HA Resorb Osteogen)

The selected chitosan-GP solution was the same as previously described in Example 3a above. Loading in synthetic nonceramic hydroxyapatite HA resorb Osteogen (Impladent Ltd., NY, USA) particles was 1:10 & 3:10 S/L (Table 9). Osteogen hydroxapatite is a dental hydroxyapatite material, about 300-400 μm in size. All chitosan-GP/Osteogen compo-

TABLE 9

Corresponding Compositions And S/L Ratios

| Liquid Component | Chitosan-GP | Chitosan-GP | chitosan-GP | chitosan-GP | Chitosan-GP | chitosan-GP |
|---|---|---|---|---|---|---|
| Solid Component | Durapatite (<125 μm) (212-250 μm) | β-TCP | HA Resorb (300-400 μm) | Apafill-G (100-400 μm) | Coralina (400-800 μm) | BCP |
| Composition | HA | β-TCP | Synthetic HA | HA | Coralline HA | HAP/β-TCP |
| S/L ratio (load) | 0:10-7:10 | 0:10-7:10 | 0:10-3:10 | 0:10-3:10 | 0:10-3:10 | 0:10-5:10 | a) Composition with Durapatite Hydroxyapatite

Figure 10:
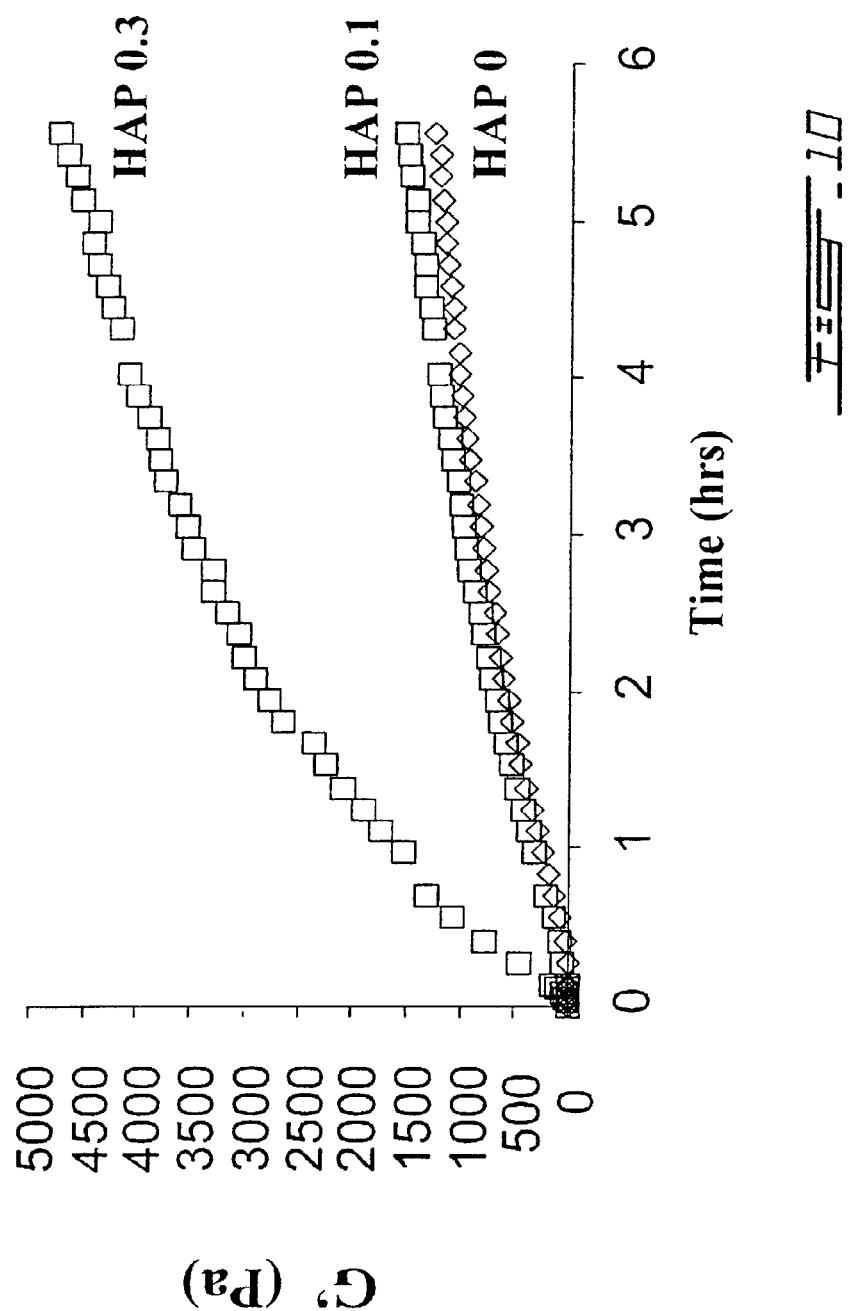
FIG. 10 illustrates the evolution of the G' modulus of CGP systems loaded with HAP (chitosan 2% w/v; GP 8.2% w/v) for a gelling at 37° C.
Figure 11:
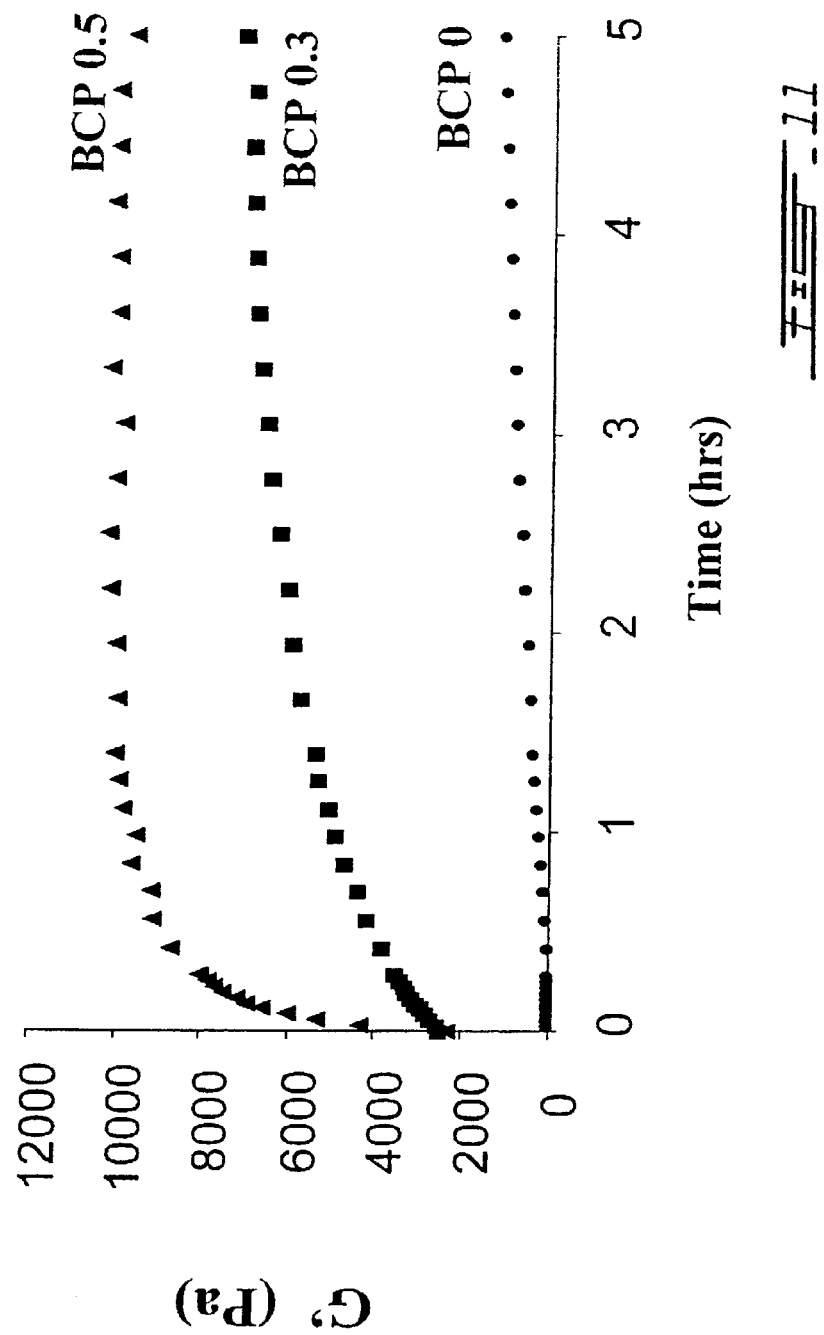
FIG. 11 illustrates the evolution of the G' modulus of CGP systems loaded with BCP (chitosan 2% w/v; GP 8.2% w/v) for a gelling at 37° C.
Figure 12A:
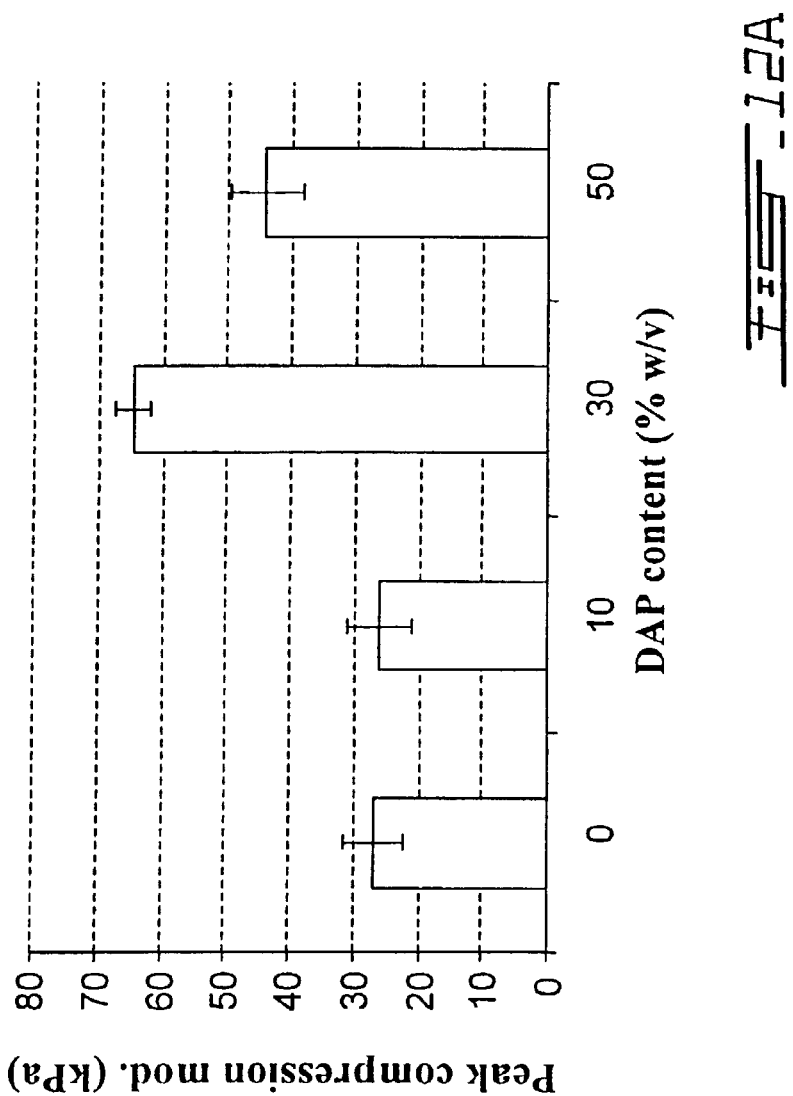
FIG. 12 illustrates the compression modulus of DAP-CGP hybrid systems as measured from stress-relaxation tests, such as comp. modulus at peak (maximal, 25% compression, 1.0%/s rate)(FIG. 12A) and comp. modulus at equilibrium (FIG. 12B)
Figure 12B:
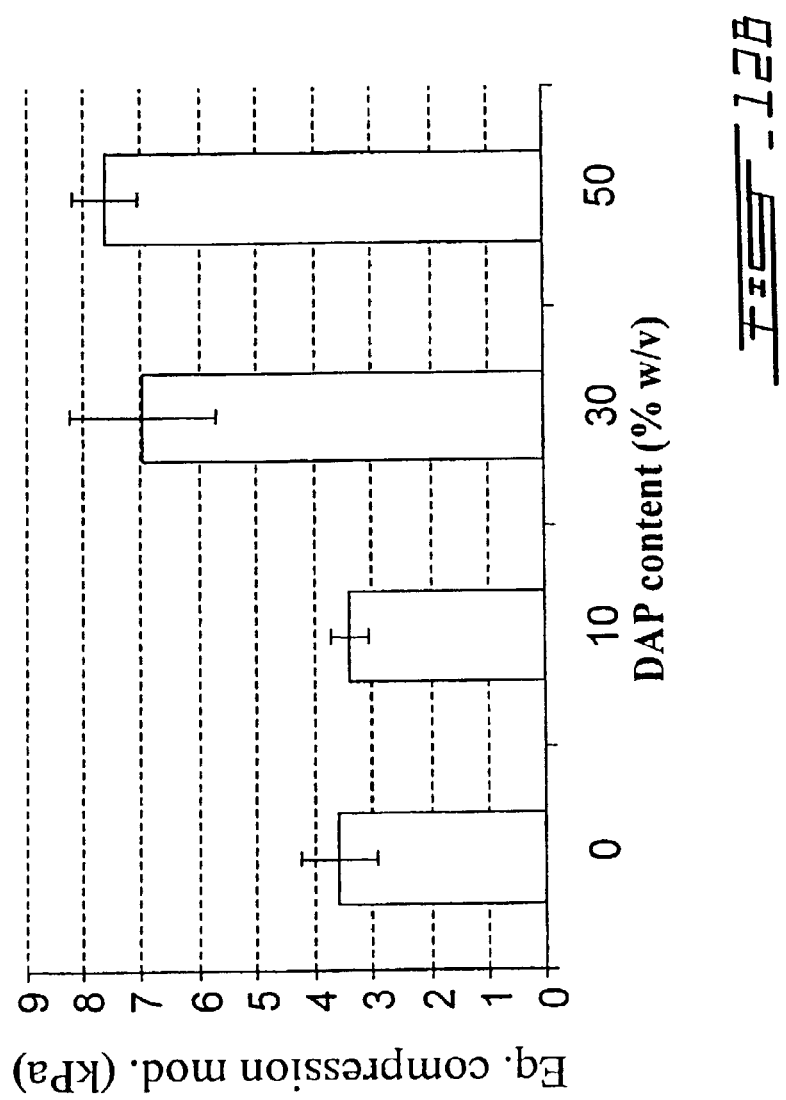
Figure 13:
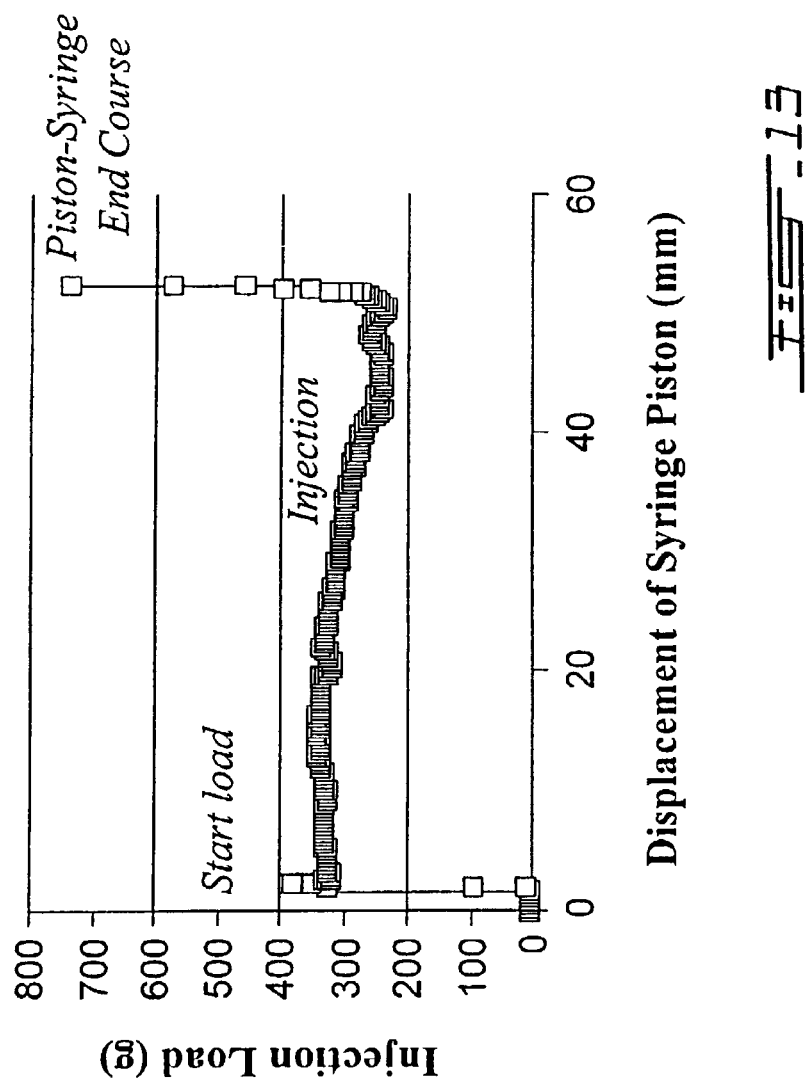
FIG. 13 illustrates the compression load for a 10 mL syringe injectability for a composition of chitosan 1.5%, GP 8.0%, HAP 30%.
Figure 14:
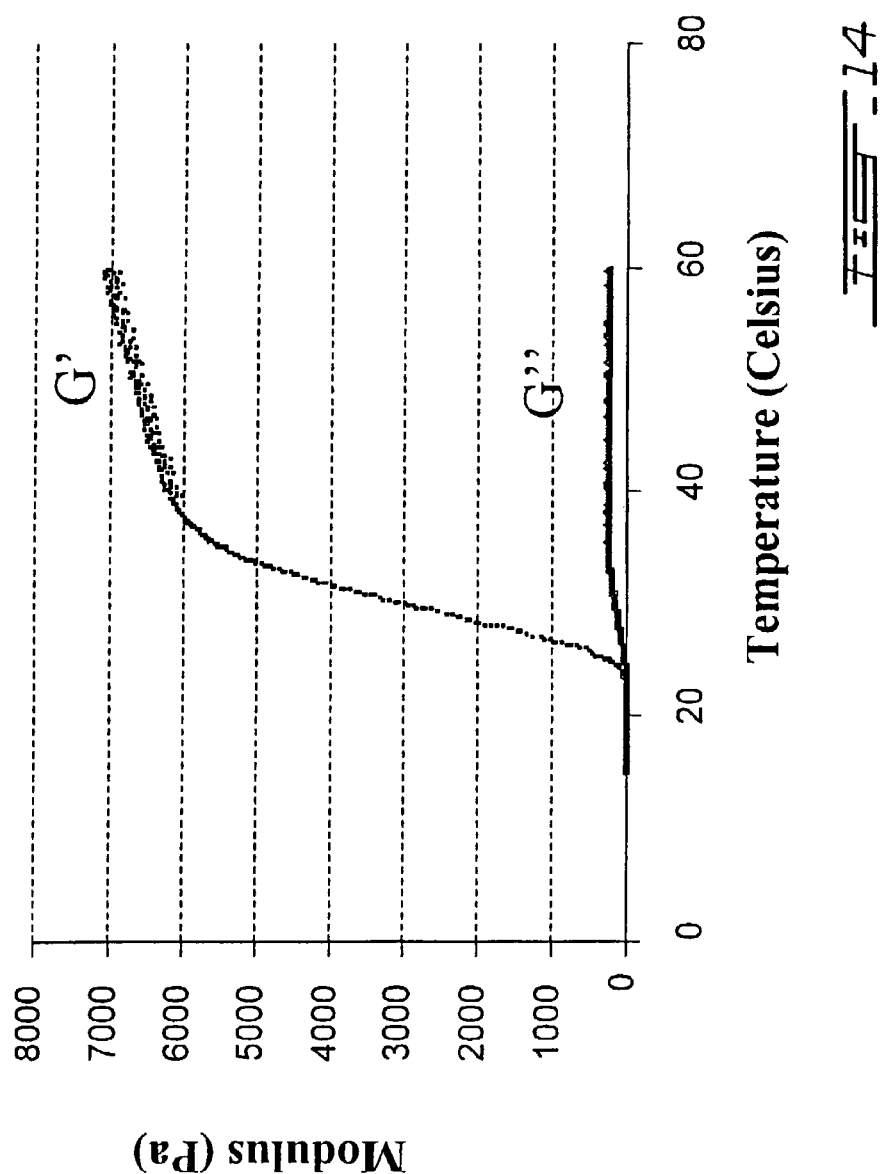
FIG. 14 illustrates the gelling with an increasing temperature of a hybrid formulation after being prepared by a two-syringes mixing for a composition containing 5 g BCP in 5 mL $H_2O$/GP (FIG. 14A) and 5 mL chitosan 4% w/v (FIG. 14B) where final concentrations were chitosan 2.0%, GP 9.0% and BCP 50% w/v
Figure 15:
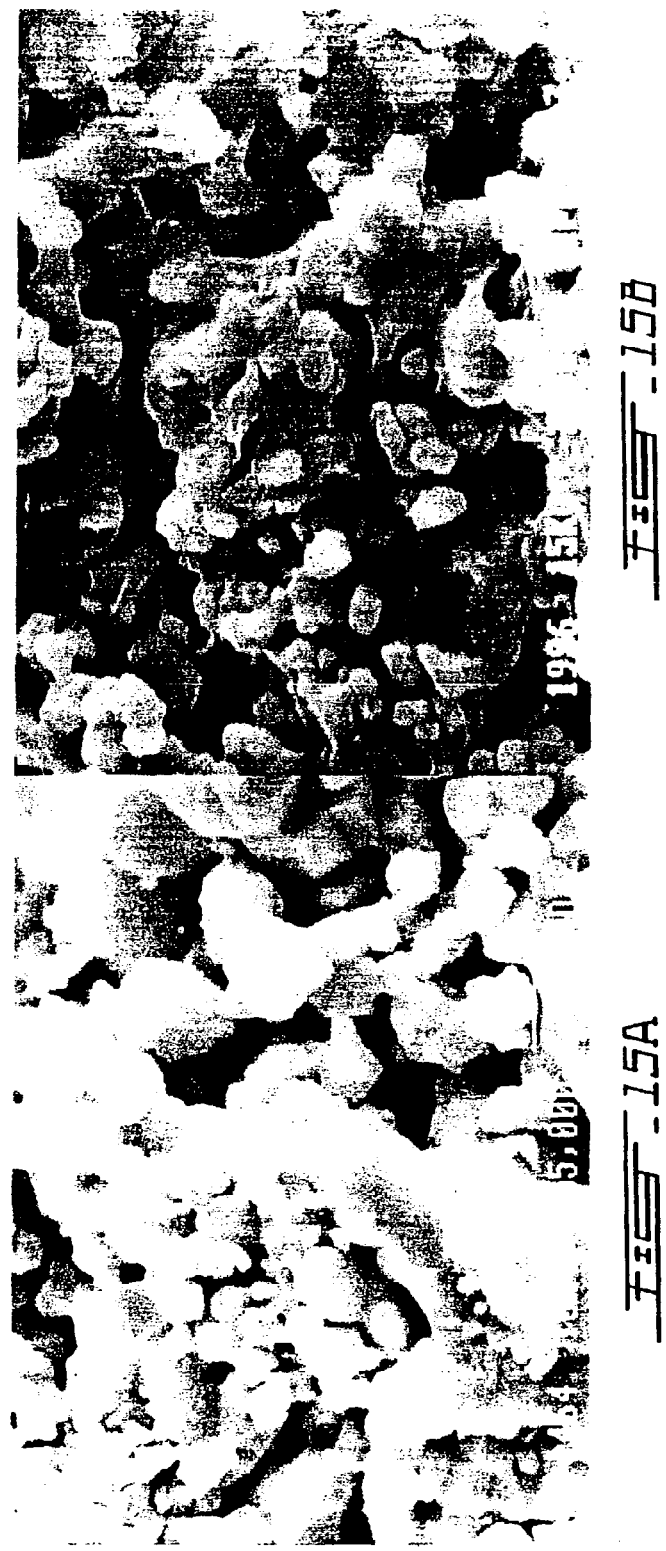
FIG. 15 illustrates the scanning electron microscopic view of BCP granules sieved at 100-250 microns (FIG. 15A) and the corresponding hybrid materials with a chitosan-glycerophosphate liquid component (FIG. 15B), where concentrations were chitosan 2.0%, GP 8.0% w/v.
Figure 16:
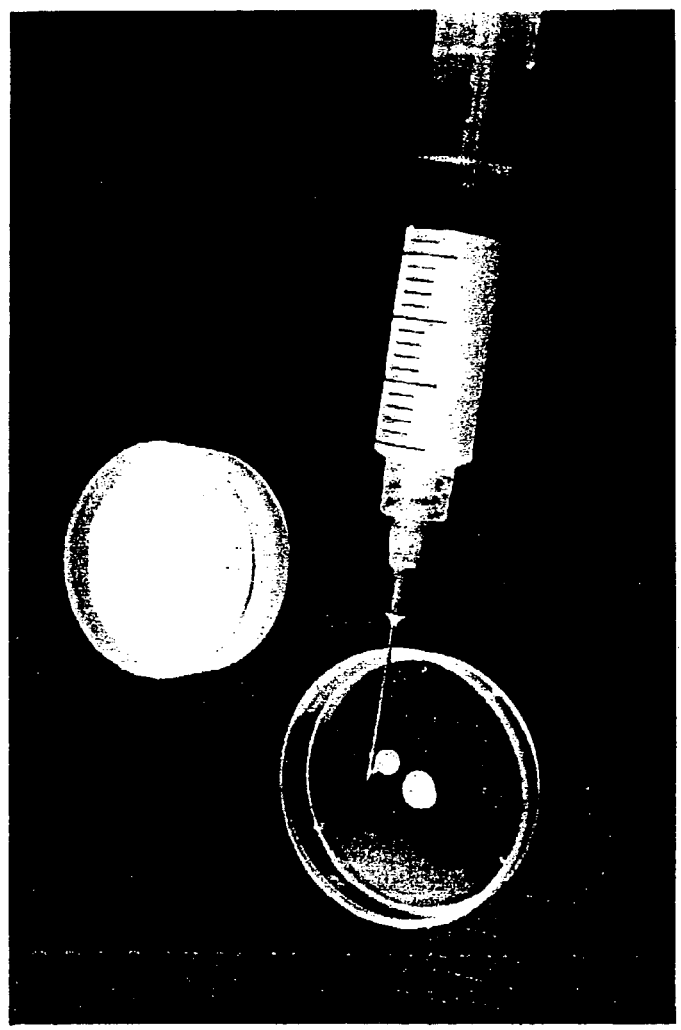
FIG. 16 illustrates the macroscopic view of the thermo-gelling polymer-mineral composition (chitosan-glycerophosphate-BCP) ready-to-use in a syringe, the composition being highly injectable, when in its liquid (ungelled) state, the composition being easily shaped and gelled in any recipient (gel state in the petri dish)

A chitosan-GP formulation basis was obtained first by preparing a 2.3% w/v chitosan (84% deacetylation) in 0.1 M HCl solution, and then by admixing the desired amount of a 55% w/v disodium glycerophosphate in distilled water solution. Final concentrations in the clear liquid chitosan-GP formulation were 2.0% w/v chitosan and 8.0% w/v glycerophosphate. Loading in solid Durapatite particles was detersitions were monitored by viscosimetric and rheologic methods, and formed solid hybrid gels at 37° C. (FIGS. 10 and 13).

d) Hybrid Materials with Hydroxyapatite Ceramic Dense Granules (Apafill-G)

The selected chitosan-GP solution was the same as previously described in Example 3a above. Loading in dense Apafill-G hydroxyapatite (BIOMAT, Habana, Cuba) particles was 3:10 S/L (Table 9). Apafill-G hydroxapatite is an orthopaedic and dental hydroxyapatite material, about 100-400 μm in size. All chitosan-GP/Apafill compositions were monitored by viscosimetric and rheologic methods, and formed solid hybrid gels at 37° C.

e) Hybrid Materials with Coralline Hydroxyapatite Granules (Coralina)

The selected chitosan-GP solution was the same as previously described in Example 3a above. Loading in Coralina hydroxyapatite (Laboratorio de Biomaterales, Cuba) particles was 3:10 S/L (Table 9). Corallina hydroxapatite is produced from marine coral materials, and is used as an orthopaedic and dental nonresorbable hydroxyapatite material, about 400-2400 μm in size. All chitosan-GP/Corallina compositions were monitored by viscosimetric and rheologic methods, and formed solid hybrid gels at 37° C.

f) Hybrid Materials with Biphasic Calcium Phosphate (BCP)

The selected chitosan-GP solution was the same as previously described in Example 3a above. Particles of HAP/β-TCP (35-40:65-60) biphasic calcium phosphate (Clarkson Chromatographic Products Inc., PA, USA; and Teknimed, Vic-en-Bigorre, FRANCE) were loaded at a solid to liquid weight ratio from 1:10 to 5:10 (Table 9). BCP is about 40:60 (wt.) powder mixture of a hydroxyapatite and a β-tricalcium phosphate. All chitosan-GP/BCP compositions were monitored by viscosimetric and rheologic methods, and formed solid hybrid gels at 37° C. All materials from examples 2a to 2f gelled into solid hybrid gels or showed endothermic signs of gelation for loadings ranging typically from 0/10 to 10/10, and preferably from 0/10 to 7/10 (0 to 1 g/mL). Ideal Ca—P loading (injectability, gel uniformity . . . ) seemed generally to be around 3/10 to 5/10, however changed slightly with the Ca—P chemical nature and granulometry (size, density) (FIGS. 11, 14, 15, and 16).

g) Osteoinductive Bone Hybrid Compositions and Bio-Materials

A self-forming bone hybrid composition and bio-material was composed of chitosan-GP, hydroxyapatite and CDBP. The chitosan-GP was prepared to 1.5% (w/v) of chitosan and 8.2% (w/v) of GP. A 1.0 ml of human CDBP powder was admixed with a 10 ml of chitosan-GP solution, then loaded with 3.0 grams of Durapatite particles (200-250 μm).

The flowable resulting suspension was carefully mixed and homogenized (manually and mechanically). Gel formation was reached and controlled at 37° C.

Example IV

In Vivo Study of Bone Compositions, Bio-Materials and Related Components a) Subcutaneous Injections of Pure Liquid Components Liquid phases consisting in aqueous thermo-gelling solutions of chitosan (2.0% w/v) and glycerophosphate (8.2% w/v) were prepared sterile, by autoclaving chitosan solutions and filtering glycerophosphate solutions. Adult albino Sprague Dawley rats were anesthetized for 40 minutes by intraperitoneal injections of 2.7 mL/kg of a Hypnorm® and Midazolal (Versed®) mixture, made by mixing 1 ml of Hypnorm® and 1 ml of 5 mg/ml Midazolal with 2 ml of sterile water. Sub-cutaneous injections about 0.2 ml/injections were performed on each side of the spine mid-line. The animals were returned to normal activities. Sacrifices by carbon dioxide overdose were done at 3, 7, 14, 21, 30, 60, 90 and 120 days. Implants were collected, macroscopically examined and analyzed by histology (H&E staining on thin slides). Gross observations showed that chitosan-GP systems formed in situ cohesive matrices having spherical to ovoid shapes. Implants did not travel subcutaneously, at any times. Histological analyses showed a reduced acute inflammation, and a moderate chronic inflammation that was associated to the implant erosion. Chitosan-GP systems were found to give cohesive, shaped, and resident implants with a moderate associated inflammatory reactions. Erosion in situ of the chitosan-GP implants was progressive and peripheric. The implants and materials resided in situ for 120 days.

b) Intramuscular Injections of Pure Liquid Components

Intra-muscular injections in rats were performed with the materials and protocols that were described in Example 4a, except that injections were intramuscularly in the muscular tissues of lower limbs. Gross observations showed that chitosan-GP systems formed in situ cohesive matrices having spherical to ovoid shapes. Implants did not travel subcutaneously, at any times. Histological analyses showed a reduced acute inflammation, and a moderate chronic inflammation that was associated to the implant erosion. Chitosan-GP systems were found to give cohesive, shaped, and resident implants with a moderate associated inflammatory reactions. Erosion in situ of the chitosan-GP implants was progressive and peripheric. The implants and materials resided in situ for 80 days.

c) Osseous Injections of Pure Liquid Components

Osseous injections in a rat trancondylar model were performed with the materials and protocols described in Example 4a, except that thermo-gelling materials were disposed in transcondylar cylindrical defects.

Gross observations showed that chitosan-GP systems formed in situ cohesive matrices. Histological analyses showed a reduced acute inflammation, and a moderate chronic inflammation that was associated to the implant erosion.

d) Subcutaneous Injections of Hybrid Materials with HA Resorb

Subcutaneous injections in rats were performed with the materials and protocols that were described in Example 4a. The hybrid compositions were aqueous, and containing 2.0% w/v of chitosan, 8.2% w/v of glycerophosphate, and 30% w/v (about 3 grs crystal per 10 grs solution) of HA Resorb synthetic hydroxyapatite crystals. Chitosan-GP was prepared sterile (chitosan autoclaved; GP filtered 0.22 μm). HA Resorb crystals were sterile at admixing in the solution. Each injection was about 200 μl in volume. Hybrid implants formed in situ were cohesive, infiltrated and did not travel in situ. The implants remained in place for a period of at least 80 days.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An in situ self-forming mineral-polymer hybrid composition comprising:
   a) a water-based and thermo-gelling liquid component comprising at least one hydrosoluble cationic polymer, one organic mono-phosphate source, and optionally one water-soluble organic mono-sulfonate, mono-sulfate or mono-carboxylate source; said liquid component having a pH between 6.5 and 7.4; and
   b) a water non-soluble solid component comprising at least one of calcium, fluoride, strontium, carbonate and phosphate salts, said solid component having a particle size ranging from 5 to 1000 micrometers, wherein said composition contains 50% weight to volume or less of the solid component and said liquid component and solid component are admixed together intimately to form a non-hardening thermo-gelling hybrid composition; said hybrid composition gelling at temperature between 25° C. and 60° C., wherein said liquid component forms a homogeneous solid aqueous gel-like material.

2. The composition according to claim 1, wherein said liquid component is prepared from organic and/or inorganic acid.

3. The composition according to claim 1, wherein said polymer is a cationic hydrophilic polysaccharide bearing amino groups, selected from the group consisting of partially-deacetylated chitosans, and pure chitosan.

4. The composition according to claim 1, wherein said polymer is a partially-deacetylated chitosan with a degree of deacetylation between 30 and 99%.

5. The composition according to claim 1, wherein said liquid component comprises a second soluble polymer selected from the group consisting of, cellulosics and synthetic polymers, including collagen, methyl cellulose, hydroxyethyl cellulose, hydroxypropyl cellulose, hydroxyethyl propylcellulose, hydroxymethyl propylcellulose, poly(ethyleneoxide), poly(propylene oxide), poly(ethylene glycol), poly(vinyl pyrrolidone)poly(vinyl alcohol), or derivatives thereof, or a mixture thereof.

6. The composition according to claim 1, wherein said organic mono-phosphate, mono-sulfonate, mono-sulfate and mono-carboxylate sources of said liquid component have a basic character and a pKa between 6.0 and 7.4.

7. The composition according to claim 1, wherein said organic mono-phosphate source is selected from the group consisting of $Na_2PO_4C_3H_5(OH)_2$, $Fe_2PO_4C_3H_5(OH)_2$, $K_2PO_4C_3H_5(OH)_2$, $MgPO_4C_3H_5(OH)_2$, $MnPO_4C_3H_5(OH)_2$, $Ca_2PO_4C_3H_5(OH)_2$, $Na_2PO_7C_3H_7$, $Na_2PO_7C_4H_7$, $K_2PO_7C_4H_7$, $NaPO_7C_4H_8$, $K_2PO_7C_4H_8$, $Na_2PO_8C_5H_9$, $K_2PO_8C_5H_9$, $NaPO_8C_5H_{10}$, $KPO_8C_5H_{10}$, $Na_2PO_9C_6H_{11}$, $NaPO_9C_6H_{12}$, $K_2PO_9C_6H_{11}$, $KPO_9C_6H_{12}$, $Na_2PO_8C_6H_{13}$, $K_2PO_8C_6H_{13}$, $NaPO_8C_6H_{14}$, $KPO_8C_6H_{14}$, $Na_2PO_9C_6H_{12}$, $K_2PO_9C_6H_{12}$, $NaPO_9C_6H_{13}$, $KPO_9C_6H_{13}$, $Na_2PO_8C_{10}H_{11}$, $K_2PO_8C_{10}H_{11}$, $NaPO_8C_{10}H_{12}$, $KPO_8C_{10}H_{12}$ and derivatives, or mixtures thereof.

8. The composition according to claim 1, wherein said organic mono-phosphate source is alpha-glycerophosphate, beta-glycerophosphate, glucose-1-phosphate, glucose-6-phosphate, fructose-1-phosphate, or fructose-6-phosphate salt, or a mixture thereof.

9. The composition according to claim 1, wherein said organic mono-sulfonate source is selected from the group consisting of N-[carbamoylmethyl]-2-aminoethanesulfonate (ACES),N,N-bis[2-hydroxyethyl]-2-aminoethane-sulfonate (BES), 3-[N,N-bis(2-hydroxyethyl)amino]-2-hydroxypropane-sulfonate (DIPSO), N-[2-hydroxyethyl]piperazine-N'-propanesulfonate (HEPES), 2-[N-morpholino]ethane-sulfonate (MES), 4-[N-morpholino]-butanesulfonate (MOBS), 3-[N-morpholino]-2-hydroxypropanesulfonate (MOPSO), or N-tris[hydroxymethyl]methyl-2-aminoethanesulfonate (TES), and a mixture thereof.

10. The composition according to claim 1, wherein said liquid component further comprises bis[2-hydroxyethyl]iminotris[hydroxymethyl]methane (BIS-TRIS), or Tris[hydroxymethyl]aminomethane (TRIZMA), or a mixture thereof.

11. The composition according to claim 1, wherein said liquid component further comprises amino-acid residues or sequences, comprising histidine (HIS) or lysine (LYS) residues or sequences.

12. The composition according to claim 1, wherein said liquid component comprises organic polyol ingredient selected from the group consisting of sugar-polyols, saccharide-polyols and glycols, such as glycerol, mannitol, sorbitol, ethylene glycol oligomers, propylene glycol oligomers, fructose, glucose, and maltose.

13. The composition according to claim 1, wherein said liquid component comprises water-soluble phosphate or carbonate salts, or a mixture thereof.

14. The composition according to claim 1, wherein said liquid component has an intrinsic viscosity ranging between 5 and 100,000 mPa·s at 21° C.

15. The composition according to claim 1, wherein said solid component comprises calcium phosphate, calcium sulfate, calcium carbonate, calcium titanate, calcium acetate, calcium glycerophosphate, calcium gluconate, calcium propionate compounds or a mixture thereof.

16. The A composition according to claim 1, wherein said solid component comprises at least one calcium phosphate selected from the group consisting of $Ca(H_2PO_4)_2.H_2O$, $CaHPO_4.2H_2O$, $CaHPO_4$, $CaZn_3(PO_4)_2$, $CaZnPO_4$, $CaNaPO_4$, $Ca_2PO_4Cl$, alpha-$Ca_3(PO_4)_2$, beta-$Ca_3(PO_4)_2$, $Ca_3(PO_4)_2.H_2O$, $Ca_4(PO_4)_2O$, $Ca_8H_2(PO_4)_{6.5}H_2O$, $Ca_9(HPO_4)(PO_4)_5OH$, $Ca_{10}(PO_4)_6(OH)_{2-2x}O_x$, and $Ca_{10}(PO_4)_6(OH)_2$, and derivatives thereof.

17. The composition according to claim 1, wherein said solid component comprises hydroxyapatite and tricalcium phosphate.

18. The composition according to claim 1, wherein said solid component comprises hydroxyapatite and alpha- or beta-tricalcium phosphate, or any combination thereof.

19. The composition according to claim 1, wherein said solid component comprises from 5 to 95% wt. of hydroxyapatite and 90 to 5% wt. of alpha- or beta-tricalcium phosphate.

20. The composition according to claim 1, wherein said solid component comprises from 45-65% wt. of hydroxyapatite and 35-55% wt. of alpha- or beta-tricalcium phosphate.

21. The composition according to claim 1, wherein said solid component comprises natural mineral components including hard-tissue, enamel or dental apatite, coral or nacre.

22. The composition according to claim 1, wherein said solid component comprises additionally a carbonate compound selected from the group consisting of $Na_2CO_3$, $CaCO_3$, $K_2CO_3$, $MgCO_3$, $ZnCO_3$, $Ca_9K(PO_4)_5(CO_3)_2$, $Ca_{8.5}Na_{1.5}(PO_4)_{4.5}(CO_3)_{2.5}$, and $Ca_9(PO_4)_{4.5}(CO_3)_{1.5}$.

23. The composition according to claim 1, wherein said solid component comprises additionally a carbonated calcium phosphate.

24. The composition according to claim 1, wherein said solid component comprises additionally a fluoride compound selected from the group consisting of NaF, $Na_2Si_6F$, KF, $KSi_6F$, $CaF_2$, $MgF_2$, $ZnF_2$, and sodium fluorophosphates.

25. The composition according to claim 1, wherein said solid component comprises additionally a fluorinated calcium phosphate.

26. The composition according to claim 1, wherein said solid component comprises additionally a strontium compound.

27. The composition according to claim 1, wherein said solid component comprises additionally a strontium containing calcium phosphate.

28. The composition according to claim 1, wherein said solid component comprises natural or synthetic solid components selected from the group consisting of mineral or ceramic materials, bioglasses, polymeric and biopolymeric materials.

29. The composition according to claim 1, wherein said solid component and said liquid component have a solid/liquid weight ratio between 0.05 and 2.0 g/mL.

30. The composition according to claim 1, wherein said hybrid composition of liquid component or solid component is admixed with autologous materials selected from the group consisting of cortical or cortico-cancellous bone, whole blood and blood components, bone marrow, cells isolated from tissues, stroma cells, and hematopoietic cells.

31. The composition according to claim 1, which further comprises osteoinductive agents selected from the group consisting of growth factors, hormones, individual osteoinductive proteins and mixtures of osteoinductive proteins.

32. The composition according to claim 1, which further comprises bone derived materials including demineralized bone matrix (DBM) or powder (DBP).

33. The composition according to claim 1, which further comprises at least one growth factor selected from the group consisting of IGF, EGF, a-FGF, b-FGF, PDGF-A, PDGF-B and TGF-beta.

34. The composition according to claim 1, which further comprises at least one bone morphogenic proteins (BMP), sialoproteins, osteonectin, osteopontin, osteocalcin, calcitonin, or a mixture thereof.

35. The composition according to claim 1, which further comprises anti-resorptive, antibiotic, antiviral, antitumor, and/or immunosuppressive agent.

36. An in situ self-forming mineral-polymer hybrid composition comprising:
   a) a liquid component, comprising at least 0.5% w/v of a chitosan, 2.0% w/v of a glycerophosphate; said liquid component having a pH between 6.5 and 7.4; and
   b) a solid component comprising at least one apatite and one tricalcium phosphate, said solid component having a particle size ranging from 5 to 1000 micrometers.

37. The composition according to claim 36, wherein said liquid component additionally comprises 0 to 10% w/v of at least one of glycerol, sorbitol, mannitol, ethylene glycol oligomers or polymers, and propylene glycol oligomers or polymers.

38. The composition according to claim 36, wherein said liquid component is admixed with autologous blood, blood component or bone marrow, said autologous blood, blood component or bone marrow being at a concentration ranging from 0 to 25% w/v.

39. The composition according to claim 36, wherein said solid component is a dry mixture of at least hydroxyapatite and beta-tricalcium phosphate.

40. The composition according to claim 36, wherein said solid component additionally comprises at least a strontium containing calcium phosphate.

41. The composition according to claim 36, wherein said solid component additionally comprises 0 to 25% w/v of dry crunched autologous spongy bone.

42. The composition according to claim 36, wherein said solid component additionally comprises 0 to 55% w/v of dry demineralized bone material.

43. A method of preparation of an in situ self-forming mineral-polymer hybrid composition as described in claim 1 or 36, comprising the step of:
   a) preparing a first water-based liquid sub-component comprising at least one hydrosoluble cationic polymer, and preferably at least 0.5% w/v of a chitosan, said first sub-component being stable and stored below 10° C.;
   b) preparing a second water-based liquid sub-component comprising at least one organic mono-phosphate source, and optionally one water-soluble organic mono-sulfonate, mono-sulfate or mono-carboxylate source;
   c) preparing a solid component comprising at least one of calcium, fluoride, strontium, carbonate and phosphate salts, such as apatite and one tricalcium phosphate;
   d) admixing homogeneously said second liquid sub-component with said solid component into a stable water-based dispersion, said dispersion being stable and stored at room temperature or below; and
   e) admixing said first liquid component and said stable dispersion together intimately to form a non-hardening thermo-gelling hybrid composition,
   said hybrid composition having a pH between 6.5 and 7.4, being injectable, gelling at the body temperature and being applicable to any defect, cavity or anatomical structure of body's tissues.

44. The composition according to claim 1, wherein the liquid component is prepared from an acid selected from the group consisting of malic acid, propionic acid, phosphoric acid, organophosphoric acid, glycerophosphoric acid, lactic acid, hydrochloric acid, ascorbic acid, and acetic acid.

* * * * *